(12) United States Patent
Newman et al.

(10) Patent No.: US 8,439,501 B2
(45) Date of Patent: May 14, 2013

(54) DIAGNOSIS OF OPTICALLY IDENTIFIABLE OPHTHALMIC CONDITIONS

(75) Inventors: Richard W. Newman, Auburn, NY (US); Corinn C. Fahrenkrug, Liverpool, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 51 days.

(21) Appl. No.: 12/794,053

(22) Filed: Jun. 4, 2010

(65) Prior Publication Data

US 2010/0238404 A1 Sep. 23, 2010

Related U.S. Application Data

(60) Continuation of application No. 12/505,193, filed on Jul. 17, 2009, now Pat. No. 8,075,136, which is a division of application No. 11/224,774, filed on Sep. 13, 2005, now Pat. No. 7,575,321, which is a continuation-in-part of application No. 10/697,454, filed on Oct. 30, 2003, now Pat. No. 7,708,403.

(51) Int. Cl.
*A61B 3/00* (2006.01)
*A61B 3/10* (2006.01)

(52) U.S. Cl.
USPC .......................................... 351/200; 351/205

(58) Field of Classification Search .................. 351/200, 351/205, 206, 208, 209, 212, 222
See application file for complete search history.

(56) References Cited

U.S. PATENT DOCUMENTS

| | | | |
|---|---|---|---|
| 4,310,003 A | 1/1982 | Schlager | |
| 4,428,382 A | 1/1984 | Walsall et al. | |
| 4,445,516 A | 5/1984 | Wollnik et al. | |
| 4,889,422 A | 12/1989 | Pavlidis | |
| 5,065,767 A | 11/1991 | Maddess | |
| 5,295,495 A | 3/1994 | Maddess | |

(Continued)

FOREIGN PATENT DOCUMENTS

| DE | 19730503 | 1/1998 |
|---|---|---|
| EP | 0578908 | 1/1994 |

(Continued)

OTHER PUBLICATIONS

S. Sokol; "The Visually Evoked Cortical Potential in the Optic Nerve and Visual Pathway Disorders"; published in "Electrophysiological Testing in Diseases of the Retina, Optic Nerve, and Visual Pathway"; edited by G.A. Fishman; published by the American Academy of Ophthalmology, San Francisco, in 1990, vol. 2, pp. 105-141.

(Continued)

*Primary Examiner* — Joseph P Martinez
*Assistant Examiner* — Brandi Thomas
(74) *Attorney, Agent, or Firm* — Hiscock & Barclay, LLP

(57) ABSTRACT

An apparatus for performing multiple procedures involving the eye. The apparatus includes an imager for imaging at least a portion of an eye of a patient, a data collection apparatus for collecting a data set corresponding to at least a portion of an eye of a patient, and a data analysis module. The imager is configured to provide image data. The data collection apparatus is configured to provide data indicative of a neurological disorder. The data analysis module interrelates the image data and the data indicative of a neurological disorder to provide an interpretive result.

24 Claims, 14 Drawing Sheets

U.S. PATENT DOCUMENTS

| | | | |
|---|---|---|---|
| 5,474,081 | A | 12/1995 | Livingstone et al. |
| 5,539,482 | A | 7/1996 | James et al. |
| 5,595,883 | A | 1/1997 | Appleyard et al. |
| 5,704,369 | A | 1/1998 | Scinto et al. |
| 5,713,353 | A | 2/1998 | Castano |
| 5,778,893 | A | 7/1998 | Potter |
| 5,830,139 | A | 11/1998 | Abreu |
| 5,894,338 | A | 4/1999 | Miehle et al. |
| 5,912,723 | A | 6/1999 | Maddess |
| 6,024,450 | A | 2/2000 | Ishikawa et al. |
| 6,068,377 | A | 5/2000 | McKinnon et al. |
| 6,113,537 | A | 9/2000 | Castano |
| 6,120,460 | A | 9/2000 | Abreu |
| 6,123,668 | A | 9/2000 | Abreu |
| 6,123,943 | A | 9/2000 | Baba et al. |
| 6,129,682 | A | 10/2000 | Borchert et al. |
| 6,247,812 | B1 | 6/2001 | Miehle et al. |
| 6,305,804 | B1 | 10/2001 | Rice et al. |
| 6,312,393 | B1 | 11/2001 | Abreu |
| 6,315,414 | B1 | 11/2001 | Maddess et al. |
| 6,423,001 | B1 | 7/2002 | Abreu |
| 6,477,394 | B2 | 11/2002 | Rice et al. |
| 6,556,853 | B1 | 4/2003 | Cabib et al. |
| 6,561,992 | B1 * | 5/2003 | Eberhart et al. ............... 600/595 |
| 6,603,552 | B1 | 8/2003 | Cline et al. |
| 7,050,087 | B2 | 5/2006 | Harari et al. |
| 7,166,079 | B2 | 1/2007 | Febbroriello et al. |
| 7,232,220 | B2 | 6/2007 | Franz et al. |
| 7,237,898 | B1 * | 7/2007 | Hohla et al. ................... 351/246 |
| 7,575,321 | B2 | 8/2009 | Newman et al. |
| 7,708,403 | B2 | 5/2010 | Newman |
| 2002/0097379 | A1 | 7/2002 | Goldfain et al. |
| 2002/0106617 | A1 | 8/2002 | Hersh |
| 2003/0171320 | A1 * | 9/2003 | Guyer .............................. 514/44 |
| 2004/0105073 | A1 | 6/2004 | Maddalena et al. |
| 2005/0243277 | A1 | 11/2005 | Nashner |
| 2006/0025658 | A1 | 2/2006 | Newman et al. |
| 2009/0270717 | A1 | 10/2009 | Newman |
| 2010/0014050 | A1 | 1/2010 | Newman et al. |
| 2010/0238405 | A1 | 9/2010 | Newman et al. |

FOREIGN PATENT DOCUMENTS

| | | |
|---|---|---|
| EP | 1127534 | 8/2001 |
| EP | 1219243 | 7/2002 |
| EP | 1527731 | 5/2005 |
| FR | 2593381 | 7/1987 |
| WO | WO98/57579 | 12/1998 |
| WO | WO02/41108 | 5/2002 |
| WO | WO2004/084117 | 9/2004 |
| WO | WO2007/061469 | 5/2007 |

OTHER PUBLICATIONS

Clark Tsai; "Optic Nerve Head and Nerve Fiber Layer in Alzheimer's Disease"; published in Arch. of Ophthalmology, vol. 107, Feb. 1991.

Sarah Muscat, Stuart Parks, Ewan Kemp, and David Keating; "Repeatability and Reproducibility of Macular Thickness Measurements with the Humphrey OCT System"; published in IVOS, Feb. 2002, vol. 43, No. 2 (6 pages).

European Search Report for 06801682.3, dated Jan. 14, 2010 (15 pages).

European Search Report for 04025213.2, dated Feb. 16, 2005 (5 pages).

International Search Report for PCT/US2006/032065, dated Apr. 3, 2007 (5 pages).

Extended European Search Report for 06801682.3, dated Oct. 9, 2009 (16 pages).

Silva et al. Independent patterns of damage with magno-, parvo- and koniocellular pathways in Parkinson's disease. Brain (Oct. 2005) 128 (10); 2260-2271.

Ruseckaite et al., Frequency doubling illusion VEPs and automated perimetry in multiple sclerosis. Doc Ophtalmol. Jul. 2006; 113(10); 29-41.Epub Aug. 12, 2006.

Valenti et al., To Discuss the Deficits in the Visual Pathway of Those with Parkinson's Disease (PD) as Measured by Frequency Doubling Techology (FDT), Optical Coherence Tomography (OCT) and Magnetic Resonance Imaging (MRI). ARVO 2005 Abstracts http://www.arvo.org/EWEB/dynamicPage.aspx?WebCode=2005abstracts&site=isie.

Valenti. "Optometrist moderates ARVO panel, presents pharmacology lecture". American Optometric Association News. vol. 45 No. 16, May 14, 2007 p. 7.

* cited by examiner

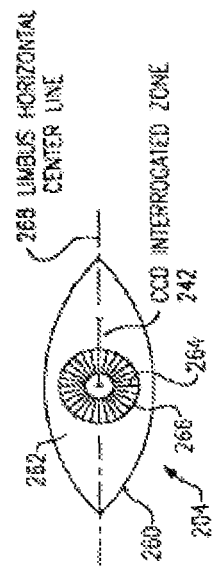
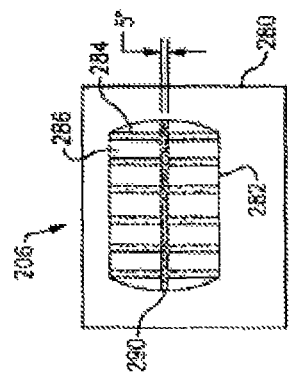
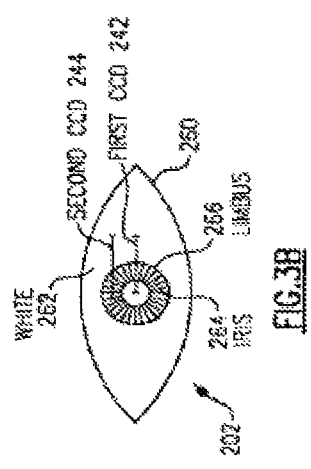
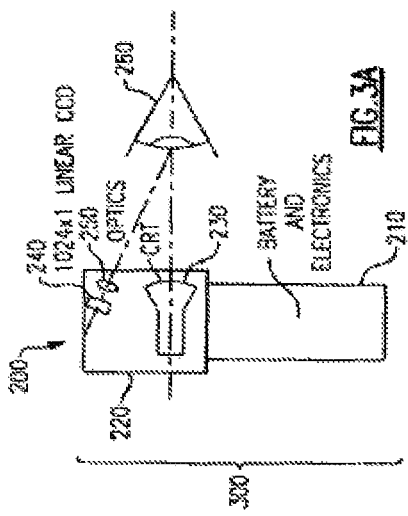

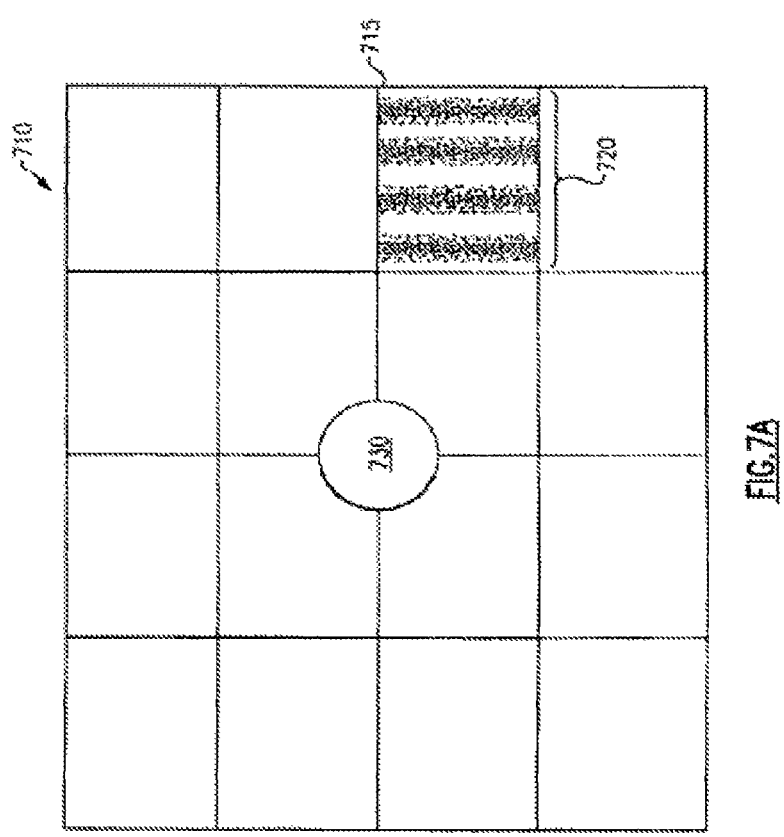

DIAGNOSIS OF OPTICALLY IDENTIFIABLE OPHTHALMIC CONDITIONS

CROSS-REFERENCE TO RELATED APPLICATIONS

This application is a continuation patent application of, and claims priority and benefit to, co-pending U.S. patent application Ser. No. 12/505,193, that was filed on Jul. 17, 2009 and entitled "Apparatus And Method for Diagnosis of Optically Identifiable Ophthalmic Conditions", which is a divisional continuation patent application of, and claims priority and benefit to, U.S. patent application Ser. No. 11/224,774 that was filed on Sep. 13, 2005, entitled "Apparatus And Method for Diagnosis of Optically Identifiable Ophthalmic Conditions", and now issued U.S. Pat. No. 7,575,321, which is a continuation-in-part application of, and claims the priority and benefit to, U.S. patent application Ser. No. 10/697,454 that was filed Oct. 30, 2003, entitled "Apparatus And Method for Diagnosis of Optically Identifiable Ophthalmic Conditions", and now issued U.S. Pat. No. 7,708,403. The patent application is being concurrently filed with U.S. patent application Ser. No. 12/793,989, entitled "Diagnosis of Optically Identifiable Ophthalmic Conditions". All of the aforementioned patent applications and patents are incorporated herein by reference in their entirety.

FIELD OF THE INVENTION

The invention relates to testing for physiological and neurological conditions in general and particularly to systems and methods that employ optical imaging of an eye and the responses of individuals to visual stimuli.

BACKGROUND OF THE INVENTION

Numerous systems and methods are known for examining states of health of eyes. For example, U.S. Pat. No. 5,065,767, issued Nov. 19, 1991 to Maddess, discloses a psychophysical method for diagnosing glaucoma that employs a time varying contrast pattern. Glaucoma may be indicated for an individual who displays a higher than normal contrast threshold for observing the pattern. Maddess also discloses other tests for glaucoma such as the well-known observation of a scotoma, measurement of intraocular pressure, and assessment of color vision defects. U.S. Pat. No. 5,295,495, issued Mar. 24, 1994 to Maddess, discloses systems and methods for diagnosing glaucoma using an individual's response to horizontally moving stripe patterns, which is known as optokinetic nystagmus (OKN). The spatially varying patterns may also vary temporally. In U.S. Pat. No. 5,539,482, issued Jul. 23, 1996 to James et al., additional systems and methods for diagnosing glaucoma using spatial as well as temporal variations in contrast patterns are disclosed. U.S. Pat. No. 5,912,723, issued Jun. 15, 1999 to Maddess, discloses systems and methods that use a plurality of spatially and temporally varying contrast patterns to improve the methods disclosed in the earlier patents. U.S. Pat. No. 6,315,414, issued Nov. 13, 2001 to Maddess et al., describes systems and methods for making a binocular assessment of possible damage to the optical nerve, optical radiations and white matter of the visual brain indicative of various neurological disorders by measuring responses to visual stimuli.

U.S. Pat. No. 6,068,377, issued May 30, 2000 to McKinnon et al., describes systems and methods for testing for glaucoma using a frequency doubling phenomenon produced by isoluminent color visual stimuli. The disclosure is similar to that of Maddess and co-workers, but uses different, preferably complementary, frequencies of light having the same luminosity as the visual probe signal.

U.S. Pat. Nos. 5,713,353 and 6,113,537 describe systems and methods for testing for blood glucose level using light patterns that vary in intensity, color, rate of flicker, spatial contrast, detail content and or speed. The approach described involves measuring the response of a person to one or more light pattern variations and deducing a blood glucose level by comparing the data to calibration data.

Other disease conditions and their identification are described in a paper by S. Sokol, entitled "The visually evoked cortical potential in the optic nerve and visual pathway disorders," which was published in Electrophysiological testing in diseases of the retina, optic nerve, and visual pathway, edited by G. A. Fishman, published by the American Academy of Opthalmology, of San Francisco, in 1990, Volume 2, Pages 105-141. An article by Clark Tsai, entitled "Optic Nerve Head and Nerve Fiber Layer in Alzheimer's Disease," which was published in Arch. of Opthalmology, Vol. 107, February, 1991, states that large diameter neurons are damaged in Alzheimer's disease.

U.S. Pat. No. 5,474,081, issued Dec. 12, 1995 to Livingstone et al., describes systems and methods for determining magnocellular defect and dyslexia by presenting temporally and spatially varying patterns, and detecting visually evoked potentials (VEP) using an electrode assembly in contact with the subject being tested.

U.S. Pat. No. 6,129,682, issued Oct. 10, 2000 to Borchert et al., discloses systems and methods for non-invasively measuring intracranial pressure from measurements of an eye, using an imaging scan of the retina of an eye and a measurement of intraocular pressure. The intraocular pressure is measured by standard ocular tonometry, which is a procedure that generally involves contact with the eye. U.S. Pat. Nos. 5,830,139, 6,120,460, 6,123,668, 6,123,943, 6,312,393 and 6,423,001 describe various systems and methods that involve mechanical contact with an eye in order to perform various tests. Direct physical contact with an eye involves potential discomfort and risk of injury through inadvertent application of force or transfer of harmful chemical or biological material to the eye. Direct physical contact with an eye is also potentially threatening to some patients, especially those who are young or who may not fully understand the test that is being performed.

First Generation FDT Instrument

The Frequency Doubling Technique (hereinafter "FDT") presents back-lit flashed images viewed on a fixed, flat shielded screen in front of a stationary subject. The FDT instrument is similar, but smaller, and the FDT test is substantially shorter in testing duration, as compared to a visual field instrument that tests peripheral and central vision. Visual field testing is standard in all offices providing comprehensive eye exams and treatment of eye disease. The FDT instrument uses sinusoidal grating targets of low spatial frequency (as opposed to simple dots of light in a traditional visual field test). The sinusoidal gratings are reversed (black to white, and white to black) at 25 Hz. The subject perceives the targets as small striped areas in either central or peripheral vision. As with traditional visual field testing, subjects are seated and have the chin and forehead positioned in a stabilizing rest support. Generally, subjects are tested monocularly. They fixate a target directly in front of them and respond by pushing a button each time they see an image flashed anywhere in their visual field. The instrument records and retests areas based on the subject's responses. A computer program operating on a processor calculates reliability based on fixation losses. The entire test takes less than two minutes per eye. The FDT does not require dilation of the subject's eyes. Therefore, it does not impair vision or the ability to function after the test is performed. The test causes no discomfort. The FDT has received approval from the Federal Drug Administration and has been in clinical use for over four years.

There is a need for systems and methods that will provide better information about a larger number of possible conditions using a single testing period, and that will disclose the initial levels of impairment at accuracies that are not presently attainable, while avoiding to the extent possible mechanical contact with the test subject, especially contact with the eye. There is also a need for systems and methods that can be used by non-specialist medical practitioners to screen and evaluate patients without the necessity to first involve a specialist practitioner.

SUMMARY OF THE INVENTION

The invention uses more than one observation selected from imaging methods and responses (e.g., a "data set") of a person to provide an assessment of a state of health or medical condition of the person. The images are obtained from any imaging method that provides image information about a portion of an eye. The responses or data sets are obtained as the response of a person to a test that elicits voluntary or involuntary responses that provide information about a neurological state or condition of the person. The invention combines or correlates information from the more than one observation to provide the assessment.

In one aspect, the invention relates to a method of obtaining an interpretive result relating to a condition of a person. The method comprises the steps of receiving at a testing venue a person whose condition is to be evaluated; testing the person at the testing venue with an apparatus having at least one imager for imaging at least a portion of an eye of the person and at least one data collection apparatus for collecting from the eye a data set indicative of a neurological disorder, the testing comprises observing with the apparatus at least two disparate kinds of information selected from one or more images and one or more data sets; and interrelating the at least two disparate kinds of information selected from one or more images and one or more data sets to obtain the interpretive result relating to the condition of the person.

In one embodiment, the at least one imager for imaging at least a portion of an eye of the person is configured to provide image data comprises at least one image data type selected from the group consisting of data from ophthalmic images using confocal microscopy data, retinal polarimetry data, optical coherence tompography data, thermal image data, spectroscopic image data, refractometry data, and visible image data. In one embodiment, the data set indicative of a neurological disorder is selected from the group consisting of data indicative of a selected one of macular degeneration, diabetic retinopathy, Parkinson's disease, Alzheimer's disease, non-Alzheimer's dementia, dyslexia, multiple sclerosis, optic neuritis, optical neuroma, ALS, head trauma, diabetes, and inappropriate responses to contrast sensitivity patterns. In one embodiment, the interpretive result comprises providing an indication of a selected one of normal health, the early (or onset) stage of the disease condition, and the development of the disease condition up to a fully presented disease condition.

In one embodiment, the method further comprises the step of recording in a memory at least one of the at least two disparate kinds of information selected from one or more images and one or more data sets. In one embodiment, the method further comprises the step of retrieving as information from the memory at least one of the at least two disparate kinds of information selected from one or more images and one or more data sets. In one embodiment, the further comprises the step of comparing retrieved information with current information to monitor a selected one of a rate of evolution and an extent of evolution of a disease condition in the person.

In one embodiment, the method further comprises the step of applying a stress to the person. In one embodiment, applying a stress to the person comprises applying a stress selected from the group consisting of an intra ocular pressure variation, a blood pressure variation, an oxygen concentration variation, performing exercise, a flashing light, an administration of a drug, an administration of insulin, and an administration of glucose. In one embodiment, the method further comprises the step of observing a response of the person to the stress on the person. In one embodiment, the method further comprises the step of observing a time evolution of the response of the person to the stress on the person.

In one embodiment, the method further comprises the step of performing a selected one of displaying the interpretive result and reporting the interpretive result. In one embodiment, the method further comprises the step of receiving financial compensation for performing a selected one of displaying the interpretive result and reporting the interpretive result.

In one embodiment, the method further comprises the step of receiving financial compensation for performing the testing.

In one embodiment, the interpretive result comprises providing an indication of a tendency to develop a disease condition.

In another aspect, the invention features a testing venue for testing a condition of a person. The testing venue comprises a venue wherein a test of a condition of a person is performed; an apparatus located at the venue having at least one imager for imaging at least a portion of an eye of the person and at least one data collection apparatus for collecting from the eye a data set indicative of a neurological disorder, the apparatus configured to obtain at least two disparate kinds of information selected from one or more images and one or more data sets with the apparatus; and a data analysis module that receives and interrelates the at least two disparate kinds of information selected from one or more images and one or more data sets to provide the interpretive result relating to the condition of the person.

In one embodiment, the at least one imager for imaging at least a portion of an eye of the person is configured to provide image data comprises at least one image data type selected from the group consisting of data from ophthalmic images using confocal microscopy data, retinal polarimetry data, optical coherence tompography data, thermal image data, spectroscopic image data, refractometry data, and visible image data. In one embodiment, the data set indicative of a neurological disorder is selected from the group consisting of data indicative of a selected one of macular degeneration, diabetic retinopathy, Parkinson's disease, Alzheimer's disease, non-Alzheimer's dementia, dyslexia, multiple sclerosis, optic neuritis, optical neuroma, ALS, head trauma, diabetes, and inappropriate responses to contrast sensitivity patterns.

In one embodiment, the testing venue further comprises a memory for recording at least one of the at least two disparate kinds of information selected from one or more images and one or more data sets with the apparatus. In one embodiment, at least one of the at least two disparate kinds of information selected from one or more images and one or more data sets recorded in the memory can be retrieved as information. In one embodiment, the data analysis module is configured to compare retrieved information from the memory with current information to monitor a selected one of a rate of evolution and an extent of evolution of a disease condition in the person.

In one embodiment, the testing venue further comprises a display for displaying the interpretive result. In one embodiment, the testing venue further comprises a reporting module for reporting the interpretive result. In one embodiment, the apparatus having at least one imager for imaging at least a portion of an eye of the person and at least one data collection apparatus for collecting from the eye a data set indicative of a neurological disorder is configured to observe a response to a stress applied to the person. In one embodiment, a stress applied to the person comprises a stress selected from the group consisting of an intra ocular pressure variation, a blood pressure variation, an oxygen concentration variation, performing exercise, a flashing light, an administration of a drug, an administration of insulin, and an administration of glucose. In one embodiment, the apparatus having at least one imager for imaging at least a portion of an eye of the person and at least one data collection apparatus for collecting from the eye a data set indicative of a neurological disorder is configured to observe a time evolution of the response of the person to the applied stress. In one embodiment, the interpretive result comprises an indication of a selected one of normal health, the early (or onset) stage of the disease condition, and the development of the disease condition up to a fully presented disease condition. In one embodiment, the interpretive result comprises an indication of a tendency to develop a disease condition.

In yet a further aspect, the invention relates to an apparatus for obtaining an interpretive result relating to a condition of a person. The apparatus comprises at least one imager for imaging at least a portion of an eye of the person configured to observe one or more images; at least one data collection apparatus for collecting from the eye a data set indicative of a neurological disorder; an analysis module comprises a programmable processor and computer software recorded on a computer-readable medium. The computer software when operating performs the steps of interrelating at least two disparate kinds of information selected from one or more images and one or more data sets to attempt to obtain an interpretive result relating to the condition of the person; (a) in the event that the attempt to obtain an interpretive result relating to the condition of the person provides a result representing a state of normal health, recording the result and terminating the analysis; and (b) in the event that the attempt to obtain an interpretive result relating to the condition of the person provides a result representing a state of health that is not normal health, attempting to distinguish a condition represented by the state of health that is not normal health; (b)(1) in the event that the attempt to distinguish the condition represented by the state of health that is not normal health is successful, reporting an interpretive result of the condition and terminating the analysis.

In one embodiment, the computer software when operating further performs the step of (b)(2) in the event that the attempt to distinguish the condition represented by the state of health that is not normal health is unsuccessful, reporting the failure to distinguish a condition.

In one embodiment, wherein the computer software when operating further performs the step of (b)(3) optionally, prompting a user of the apparatus to provide additional information about the person.

In one embodiment, wherein the computer software when operating further performs the step of (c) upon provision of the additional information about the person, iteratively repeating the interrelating step and, as appropriate, each of conditional steps (b), (b)(1), (b)(2), (b)(3) and this step (c) using the additional information provided in response to the prompting step (b)(3) in addition to the at least two disparate kinds of information selected from one or more images and one or more data sets to attempt to obtain an interpretive result relating to the condition of the person until the first to occur of: the analysis is terminated according to step (b)(1); the iteratively repeating step is performed a predetermined number of times without distinguishing the condition represented by the state of health that is not normal health; the iteratively repeating step is performed until a specified period of time elapses without distinguishing the condition represented by the state of health that is not normal health; and a user of the apparatus determines that the analysis should be terminated, and intervenes to terminate the analysis.

In one embodiment, the additional information about the person comprises at least a selected one of collecting an additional image and collecting an additional data set. In one embodiment, the additional information about the person comprises additional information from a magnetic resonance imaging (MRI) test. In one embodiment, the MRI test comprises a structural MRI test. In one embodiment, the MRI test comprises a functional MRI test. In one embodiment, the additional information about the person comprises patient history data. In one embodiment, the additional information about the person comprises vital signs data. In one embodiment, the additional information about the person comprises additional information from a positron emission tomography (PET) test. In one embodiment, the PET test comprises an FDG-PET glucose determination. In one embodiment, the PET test comprises a C-PK11195-PET test. In one embodiment, the additional information about the person comprises additional information from a brain biopsy. In one embodiment, the additional information about the person comprises additional information from a cognitive impairment test. In one embodiment, the order of performs the steps of obtaining an image, obtaining a data set indicative of a neurological disorder, and obtaining the additional information about the person is not critical, and may be performed in any order that is convenient.

In one embodiment, when the computer software is operating, step (b)(1) is performed at least a second time to attempt to distinguish a second state of health that is not normal health different from the reported state of health that is not normal health. In one embodiment, when the computer software is operating, optionally, in step (a) the apparatus provides information relating to state of normal health to a user of the apparatus. In one embodiment, when the computer software is operating, optionally, in step (b)(1), the apparatus records the interpretive result of the condition. In one embodiment, the at least one imager for imaging at least a portion of an eye of the person is configured to provide image data comprises at least one image data type selected from the group consisting of data from ophthalmic images using confocal microscopy data, retinal polarimetry data, optical coherence tompography data, thermal image data, spectroscopic image data, refractometry data, and visible image data. In one embodiment, the data set indicative of a neurological disorder is selected from the group consisting of data indicative of a selected one of macular degeneration, diabetic retinopathy, Parkinson's disease, Alzheimer's disease, non-Alzheimer's dementia, dyslexia, multiple sclerosis, optic neuritis, optical neuroma, ALS, head trauma, diabetes, and inappropriate responses to contrast sensitivity patterns. In one embodiment, the interpretive result comprises an indication of a selected one of normal health, the early (or onset) stage of the disease condition, and the development of the disease condition up to a fully presented disease condition. In one embodiment, the computer software when operating further performs the step of recording in a memory at least one of the at least two disparate kinds of information selected from one or more images and one or more data sets. In one embodiment, the computer software when operating further performs the step of retrieving as information from the memory at least one of the at least two disparate kinds of information selected from one or more images and one or more data sets. In one embodiment, when the computer software when operating further performs the step of comparing retrieved information with current information to monitor a selected one of a rate of evolution and an extent of evolution of a disease condition in the person. In one embodiment, the computer software when operating further performs the step of applying a stress to the person. In one embodiment, applying a stress to the person comprises applying a stress selected from the group consisting of an intra ocular pressure variation, a blood pressure variation, an oxygen concentration variation, performing exercise, a flashing light, an administration of a drug, an administration of insulin, and an administration of glucose. In one embodiment, the computer software when operating further performs the step of observing a response of the person to the stress on the person. In one embodiment, the computer software when operating further performs the step of observing a time evolution of the response of the person to the stress on the person. In one embodiment, the computer software when operating further performs the step of performing a selected one of displaying the interpretive result and reporting the interpretive result. In one embodiment, the interpretive result comprises an indication of a tendency to develop a disease condition. In one embodiment, the computer software when operating repeats its operation for data relating to a second eye of the person to determine a condition of health of the person. In one embodiment, the condition of health of the person obtained from data from one of the first eye of the person and the second eye of the person is used as a baseline condition for a later testing of the other of the first eye of the person and the second eye of the person.

In an additional aspect, the invention features an apparatus for obtaining an interpretive result relating to a condition of a person. The apparatus comprises at least one data collection apparatus for collecting from the eye a data set indicative of a neurological disorder; an analysis module comprising a programmable processor and computer software recorded on a computer-readable medium, the computer software when operating performing the steps of: attempting to obtain from the one or more data sets an interpretive result relating to the condition of the person; (a) in the event that the attempt to obtain an interpretive result relating to the condition of the person provides a result representing a state of normal health, recording the result and terminating the analysis; and (b) in the event that the attempt to obtain an interpretive result relating to the condition of the person provides a result representing a state of health that is not normal health, attempting to distinguish a condition represented by the state of health that is not normal health; (b)(1) in the event that the attempt to distinguish the condition represented by the state of health that is not normal health is successful, reporting an interpretive result of the condition and terminating the analysis.

In one embodiment, the computer software when operating further performs the step of: (b)(2) in the event that the attempt to distinguish the condition represented by the state of health that is not normal health is unsuccessful, reporting the failure to distinguish a condition. In one embodiment, the computer software when operating further performs the step of: (b)(3) optionally, prompting a user of the apparatus to provide additional information about the person. In one embodiment, the computer software when operating further performs the step of: (c) upon provision of the additional information about the person, iteratively repeating the inter-relating step and, as appropriate, each of conditional steps (b), (b)(1), (b)(2), (b)(3) and this step (c) using the additional information provided in response to the prompting step (b)(3) in addition to the one or more data sets to attempt to obtain an interpretive result relating to the condition of the person until the first to occur of: the analysis is terminated according to step (b)(1); the iteratively repeating step is performed a predetermined number of times without distinguishing the condition represented by the state of health that is not normal health; the iteratively repeating step is performed until a specified period of time elapses without distinguishing the condition represented by the state of health that is not normal health; and a user of the apparatus determines that the analysis should be terminated, and intervenes to terminate the analysis.

In one embodiment, the additional information about the person comprises collecting an additional data set. In one embodiment, the additional information about the person comprises additional information from a magnetic resonance imaging (MRI) test the MRI test comprises a structural MRI test. In one embodiment, the MRI test comprises a functional MRI test. In one embodiment, the additional information about the person comprises patient history data. In one embodiment, the additional information about the person comprises vital signs data. In one embodiment, the additional information about the person comprises additional information from a positron emission tomography (PET) test. In one embodiment, the PET test comprises an FDG-PET glucose determination. In one embodiment, the PET test comprises a C-PK11195-PET test. In one embodiment, the additional information about the person comprises additional information from a brain biopsy. In one embodiment, the additional information about the person comprises additional information from a cognitive impairment test. In one embodiment, the order of performing the steps of obtaining a data set indicative of a neurological disorder and obtaining the additional information about the person is not critical, and may be performed in any order that is convenient. In one embodiment, when the computer software is operating, step (b)(1) is performed at least a second time to attempt to distinguish a second state of health that is not normal health different from the reported state of health that is not normal health. In one embodiment, when the computer software is operating, optionally, in step (a) the apparatus provides information relating to state of normal health to a user of the apparatus. In one embodiment, when the computer software is operating, optionally, in step (b)(1), the apparatus records the interpretive result of the condition. In one embodiment, the data set indicative of a neurological disorder is selected from the group consisting of data indicative of a selected one of macular degeneration, diabetic retinopathy, Parkinson's disease, Alzheimer's disease, non-Alzheimer's dementia, dyslexia, multiple sclerosis, optic neuritis, optical neuroma, ALS, head trauma, diabetes, and inappropriate responses to contrast sensitivity patterns. In one embodiment, the interpretive result comprises an indication of a selected one of normal health, the early (or onset) stage of the disease condition, and the development of the disease condition up to a fully presented disease condition. In one embodiment, the computer software when operating further performs the step of recording in a memory at least one or more data sets. In one embodiment, the computer software when operating further performs the step of retrieving as information from the memory at least one or more data sets. In one embodiment, the computer software when operating further performs the step of comparing retrieved information with current information to monitor a selected one of a rate of evolution and an extent of evolution of a disease condition in the person. In one embodiment, the computer software when operating further performs the step of applying a stress to the person. In one embodiment, applying a stress to the person comprises applying a stress selected from the group consisting of an intra ocular pressure variation, a blood pressure variation, an oxygen concentration variation, performing exercise, a flashing light, an administration of a drug, an administration of insulin, and an administration of glucose. In one embodiment, the computer software when operating further performs the step of observing a response of the person to the stress on the person. In one embodiment, the computer software when operating further performs the step of observing a time evolution of the response of the person to the stress on the person. In one embodiment, the computer software when operating further performs the step of performing a selected one of displaying the interpretive result and reporting the interpretive result. In one embodiment, the interpretive result comprises an indication of a tendency to develop a disease condition. In one embodiment, the computer software when operating repeats its operation for data relating to a second eye of the person to determine a condition of health of the person. In one embodiment, the condition of health of the person obtained from data from one of the first eye of the person and the second eye of the person is used as a baseline condition for a later testing of the other of the first eye of the person and the second eye of the person. In one embodiment, the condition of health of the person is obtained from data relating to both the first eye of the person and the second eye of the person.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 3A shows a schematic diagram of the disposition of an eye monitoring device relative to an eye of a person being tested according to the invention;

FIG. 3B shows a diagram that depicts the interrelationship among the features of an eye of a person being tested, and the areas of the eye sensed by two sensors, according to the invention;

FIG. 3C shows a diagram that depicts the interrelationship between the features of an eye of a person being tested, and the areas of the eye sensed by one sensor, according to the invention;

FIG. 3D shows a diagram that depicts a test pattern and a fixation signal that is useful for fixating an eye of a person being tested when one sensor is employed in the eye monitoring device, according to the invention;

FIGS. 7A and 7B are drawings that depict a display space that is segmented and includes an illustrative contrast pattern, as is known in the prior art;

DETAILED DESCRIPTION OF THE INVENTION

Figure 1A:
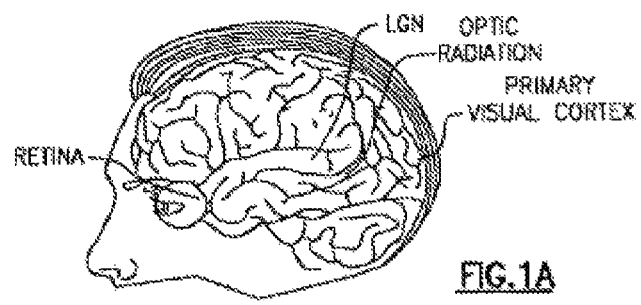
FIG. 1A is a prior art diagram showing some of the physiology of the eye and the brain in humans.

The invention provides systems and methods for determining a wide range of possible medical conditions, including normal health, the early (or onset) stage of a disease condition, and the development of the disease condition up to a fully presented disease conditions (e.g., diagnosis, staging, and monitoring). The invention provides the ability to diagnose the severity of various disease conditions. By application of the methods of the invention over time, one can monitor the rate and extent of evolution of various disease conditions in a particular individual.

The invention uses a combination of two or more observations, which can include an image of at least a portion of an eye of a patient, and a data set corresponding to a response from at least a portion of an eye of a patient. The two or more observations can comprise two images, an image and a data set, or two data sets. Images and data sets will be referred to generally as information, which should be understood as necessary to mean either images or data sets or both. The images include visualization of a portion of an eye, and can include ophthalmic images using confocal microscopy data, retinal polarimetry data, optical coherence tompography data, thermal image data, spectroscopic image data, refractometry data, and visible image data. The data sets include data that is indicative of neurological disorders. For example, the neurological disorders include glaucoma, macular degeneration, diabetic retinopathy, Parkinson's disease, Alzheimer's disease, dyslexia, multiple sclerosis, optic neuritis, and inappropriate responses to contrast sensitivity patterns. In some embodiments, the images are visible images that include color fundus photography and black and white fluorescein angiography.

The functional deficits of glaucoma and Alzheimer's Disease (hereinafter "AD") include loss in low spatial frequency ranges in contrast sensitivity, and are similar in both diseases. Glaucoma, unlike AD, involves losses of optic nerve fiber layer originating in the retina. At present, the only definitive diagnosis of AD involves identifying amyloid plaques and neuro-fibrillary tangles in the neurons of the cortex by microscopic analysis of brain tissue. The invasive nature of the test necessitates that the test be performed after death. A test specific for low spatial frequency deficits, as is available for diagnosing glaucoma, would be useful in measuring similar deficits in AD. The Frequency Doubling Technique (hereinafter "FDT"), unlike many other tests of visual function, does not require a high degree of concentration or of cognition. Because FDT takes only two minutes to administer to both eyes, it is appropriate for subjects who have difficulty concentrating for long periods.

Visual Deficits and Cognitive Function

Visual dysfunction appears to be a strong predictor of cognitive dysfunction in subjects with AD. Pattern masking has been found to be a good predictor of cognitive performance in numerous standard cognitive tests. The tests found to correlate with pattern masking included Gollin, Stroop-Work, WAIS-PA, Stroop-Color, Geo-Complex Copy, Stroop-Mixed and RCPM. Losses in contrast sensitivity at the lowest spatial frequency also was predictive of cognitive losses in the seven tests. AD subjects have abnormal word reading thresholds corresponding to their severity of cognitive impairment and reduced contrast sensitivity in all spatial frequencies as compared to normal subjects.

Review of the Physiology of Vision

The visual system is believed to be made up of two parallel pathways: the M pathway and the P pathway. The pathways have individualized function. There are a total of approximately 160 million rod and cone cells in the normal eye. There are approximately 1.2 million ganglion cells (M and P cells) in the normal eye. The magnocellular or M pathway (comprising M cells) is sensitive to contrast sensitivity and motion. M cells comprise both My cells (usually associated with contrast sensitivity) and Mx cells (usually associated with motion). There are estimated to be approximately 12,000 cells of the My type in the normal eye. The magnocellular M system has high contrast gain and saturates at relatively low contrasts. The parvocellular or P pathway (comprising P cells) is specialized for processing color and form. The parvocellular P system has a low contrast grain and more linear contrast visual stimuli. Losses specific to the M pathway have been identified in subjects with AD even in brain areas devoid of plaques and neurofibriallary tangles. The M pathway shows signs of significant cell loss in AD subjects. In studies of primates, lesions have been found in the magnocellular layers of the lateral geniculate nucleus that does not impact contrast sensitivity for stationary gratings. However, such lesions do impact sensitivity for events involving motion or high temporal content. It has been found in primates that lesions identified in the parvocellular layers of the lateral geniculate nucleus (LGN) impacted contrast sensitivity for stationary or low temporal content events.

Review of the Pathology of Glaucoma

Glaucoma is a disease that is categorized by increasing internal eye pressure on the optic nerve. The compression of the nerve causes nerve fiber morbidity and eventually cell loss. It is believed that the M ganglion cells of the visual system are impacted to a greater extent than the P cells in glaucoma. M cells are fewer in number, have larger axon diameter and larger receptive fields. Measurements of the visual field, measurements of intraocular pressure and observation of changes in the nerve fiber layer and optic disc are utilized to diagnosis and manage glaucoma. In glaucoma, the location of optic nerve change and pallor corresponds to location and density of visual field loss. New technologies that detect image losses in the nerve fiber layer may have the ability to detect glaucoma damage prior to the appearance of measurable visual field losses.

Contrast sensitivity function is frequently reduced in glaucoma. There is a high correlation of low spatial frequency contrast sensitivity loss and the mean visual field loss in glaucoma. Higher rates of glaucoma have been found among patients with AD compared to a control group. The diagnosis of glaucoma was based on the visual field defects or optic nerve cupping. Higher rates of glaucoma have also been found among patient's diagnosed with Parkinson's disease.

Visual field loss is a definitive sign of glaucoma and loss in visual field correlates with loss in contrast sensitivity. The appearance of optic nerve fiber loss detected either by observation of the fundus of the eye or by the application of newer technologies also correlates with visual field losses. The technology of the present invention may detect losses in visual field at earlier stages than the traditional instrumentation of visual field loss can measure the losses. The conclusion that optic nerve appearance and loss in the nerve fiber layer would correlate with loss in contrast sensitivity is a reasonable one in the case of glaucoma. Other diseases that have losses in contrast sensitivity also have losses in the nerve fiber layer and changes in optic nerve appearance.

Frequency Doubling Technology and Glaucoma

FDT has been shown to detect glaucomatous changes at earlier stages than are detected with stereophotographs, and has better sensitivity and specificity than motion-automated perimetry. FDT is a better predictor of progressive field loss as measured by standard automated perimetry than pattern electroretinography in a population of chronic open angle glaucoma. FDT is useful for detection of early glaucomatous visual field damage as compared to a Humphrey Field Analyzer and a high pass resolution perimeter.

In the FDT instrument, the sinusoidal gratings are reversed (black to white, and white to black) at 25 Hz. This stimulates the My ganglion cells. The contrast between the light and dark lines in the sinusoidal grating targets is changed in order to determine a threshold of perception of the target which is related to the healthy My type ganglion cells of the retina. A standard visual field test stimulates all ganglion cell types. It is believed that the My cells are the first ganglion cells to die in glaucoma. Therefore, FDT provides earlier detection of glaucoma. Subjects with AD have reductions in low spatial frequency, the same function that the FDT tests. The same cells may be impacted by AD compared to glaucoma, but the mechanism of cell death differs.

Review of the Pathology of AD

There has long been controversy as to the primary cause of AD visual symptoms. It is well documented that there are contrast sensitivity reductions, in particular at low spatial frequencies, in AD. Abnormal visual perception and abnormal visuospatial processing are common with patients diagnosed as having AD.

AD is a progressive degenerative disease of the brain leading to senility and dementia. It is known to affect millions of people and the numbers are rapidly growing. There are numerous forms of dementia, AD being only one, albeit the most devastating. Cognitive questionnaires do not accurately separate AD from other forms of dementia.

Numerous pharmaceutical companies are working on treatments for AD that will slow the progression and, in some cases, reverse the effects of AD. What is needed is a definitive, non-invasive test for AD prior to death.

AD is a large diameter neuron disease (Tsai 1991). Some researchers have found microscopic amyloid plaques on retinal ganglion cells, but not in all cases, and not at all stages of the disease. Sadun (1990) found loss in M-type retinal ganglion cells, contrast sensitivity, and visual fields in the absence of plaques or tangles, but other researchers were unable to reproduce these findings, suggesting that there is a progression in the disease with varying symptoms. Most researchers agree that amyloid plagues and tangles on cortical neurons is definitive of AD. Because a longitudinal study on suspect AD patients is impossible due to the invasiveness of the procedure, the progression of AD is not understood in detail.

Documentation of Retinal Ganglion

The degeneration in the retinal ganglion cells (RGC) of patients with Alzheimer's Disease was identified using histopatholic measure. Sadun found degeneration of the retinal ganglion cells and axonal degeneration upon examining the retro bulbar optic nerves. There was a greater frequency of degeneration the more posterior the nerve was located. A possible implication is that the retinal ganglion cell loss may be secondary to retrograde axonal degeneration.

Nerve Fiber Layer Analysis

A significant reduction in nerve fiber thickness in AD subjects compared to normal subjects has been observed using OCT Humphreys.

The present invention provides novel systems and methods for non-invasively diagnosing and tracking AD, based on a new theory of the progression of AD. In one aspect of the theory, the optic nerves are an extension of the brain and therefore provide a window to the workings of the brain. In one embodiment, the Welch Allyn Frequency Doubled Technology (FDT) visual field exam isolates retinal ganglion cells of the My type. These cells are associated with contrast sensitivity. Due to their large diameter, they are generally, though not universally, believed to be some of the first cells to die in glaucoma. Presumably, the ganglion cells are damaged by an ischemic effect when passing though bent lamina cribrosa as a result of elevated intra-ocular pressure (IOP).

FDT has become the gold standard for early diagnosis and tracking of glaucoma. Anecdotally, FDT has produced false positive diagnoses of glaucoma, when subsequent analysis indicated diagnoses of tumor, macular degeneration, diabetic retinopathy, multiple sclerosis, and other neurological diseases.

In addition, various researchers have suggested that glaucomatous damage may extend beyond the retinal ganglion cells into the lateral geniculate nucleus (LGN) and the visual cortex, and that the frequency doubled illusion may be mediated by a cortical loss of temporal phase discrimination, thus again suggesting that neuron involvement is not limited to ganglion cells.

Figure 1B:
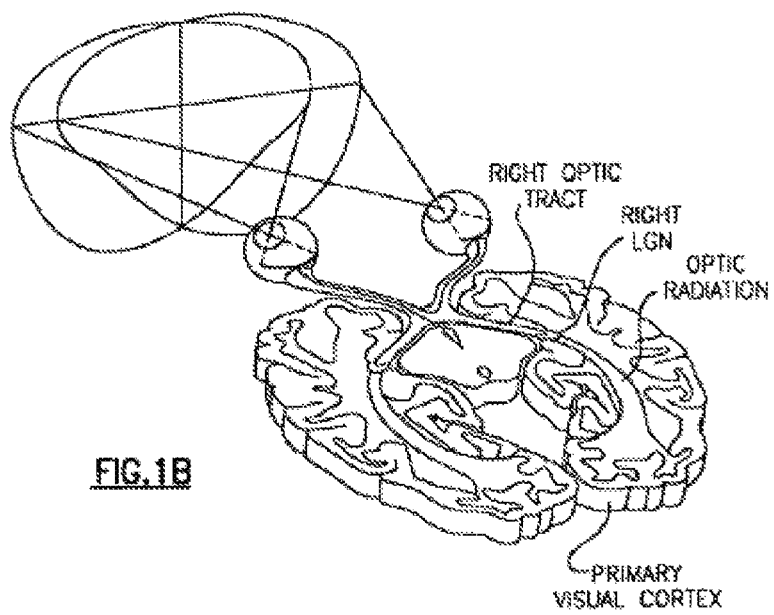
FIG. 1B depicts a prior art cross sectional diagram showing a feedback loop from the visual cortex to the LGN.

FIG. 1A is a prior art diagram showing some of the physiology of the eye and the brain in humans. FIG. 1B is a prior art cross sectional diagram showing a feedback loop from the visual cortex to the LGN. In fact, approximately 80% of the axons feeding the LGN come from the visual cortex, while approximately 20% come from the retina.

Clinical evaluations are currently underway to determine the efficacy of using FDT to diagnose and track AD. One unanswered question is whether FDT should be optimized to increase sensitivity and specificity. Although My cells are likely involved in AD, other forms of ganglion cells are also likely involved, such as Mx cells and P cells. Thus, the FDT zone shapes and sizes, spatial frequency, and temporal frequency may be optimized to isolate different forms of ganglion cells and their interaction with feedback neurons from the visual cortex. At early stages of the disease, plaques and tangles likely form in the visual cortex, thus sending an abnormal feedback to the LGN. This corticofugal feedback affects the signals from the retina leading through the LGN to the visual cortex. The result is an abnormal FDT finding. This effect may or may not be associated with ganglion cell damage caused by atrophy at a given stage in the disease. The exact etiology will only be known for certain after cross-sectional and longitudinal clinical evaluations are performed with subsequent histological analysis of the neurons. The mechanism for ganglion cells loss will likely differ from glaucoma in that there need not be elevated IOP in AD.

Similarly, it is believed that other neurological disorders (such as macular degeneration, diabetic retinopathy, optic neuritis, pappilledema, anterior ischemic optic neuropathy, and tumor) can be diagnosed and tracked by optimizing FDT (A Primer for Frequency Doubling Technology, Johnson, 1998). AD and Parkinson's were not mentioned in this product literature and are the subject of this treatise and latest invention. An improved FDT technology, hereinafter FDT2, may be a better, though slower, test for AD in that there are significantly smaller interrogated areas than in the original FDT, thus leading to detection of loss at an earlier stage and more accurate tracking of AD. FDT2 can achieve resolution that is impossible with FDT, thereby providing results that could not have been provided heretofore.

It is believed that at some point before the disease process has advanced to the stage where AD can be diagnosed using present day methods, functional vision losses associated with AD becomes apparent in the optic nerve, nerve fiber layer and retina. In one embodiment, the retina includes the peripheral retina. A variety of nerve fiber imaging techniques and photographic techniques have demonstrated changes in the optic nerve of subjects with AD. However, subjective testing relying on visual fields and perimetry techniques prove unreliable in AD subjects because of poor attentive skills. The FDT2 is a modified visual field test of short duration. Additionally, low spatial frequency targets are used to sample test areas. This FDT2 instrument has the ability to measure field losses in AD subjects as well as localize retinal areas exhibiting low spatial frequency deficits.

Studies of the visual symptoms of AD findings observed in brain lesions have shown that damage occurs in the visual association cortex and other cortical areas, as well as the primary visual cortex.

It is believed that at some point other than early in the disease process, losses associated with AD become apparent in the optic nerve and nerve fiber layer. Because it is a low spatial frequency test, the FDT will pick up such losses unlike other subjective testing such as traditional visual field techniques. The source of degeneration in the visual system does not likely originate at the level of the retinal ganglion cells. However, it seems these tissues are not spared in AD. It has long been demonstrated that pathologies originating in the higher areas of brain function eventually appear as pathology to the optic disc and nerve fiber layer. It has been shown by means of stereo photos that loss in the optic disc and nerve fiber layer are measurable in AD at some stage.

There is evidence that there are right and left field advantages for some visual functions. Because the FDT is a test of function in many ways similar to a standard visual field, it is possible to test split visual fields and therefore isolate in each eye right retinal function and left retinal function. It is also possible to compare the function of the right eye to the function of the left eye.

Histopathology studies of the optic nerve of subjects with AD were thought to show axonal degeneration originating from the retina. There is a loss of both large and small diameter ganglion cell layer neurons. These studies concluded there is a greater drop out of the larger neurons which project to the M layers of the lateral geniculate nucleus. Based on studies of primate retina and visual function, if there is a loss of cells along the M pathway, it would be expected that there would be reductions in the ability to perceive motion or high temporal content events. Several studies of AD subjects have reported this. Indirect comparisons of losses in both the P channels and the M channels showed that the M channel function deteriorates at a greater rate than the P channel function in AD.

The Present Invention

It is believed that the optic nerves, as direct and intimate extensions of the brain, are likely to be among the earliest nerves to exhibit changes associated with various neurological disorders. It is believed that these neurological disorders are observable by imaging the eye and measuring changes (or deviations) therein from what is considered normal, as well as in neurological responses that are manifested in the behavior and response of the eye, including the retina and the optic nerves. In addition, objective tests such as OKN, VEP and pattern electroretinograms (PERG) can be implemented in the systems and methods of the invention. Objective tests are useful with infants and geriatrics, as well as those who have difficulty communicating or following specific directions.

Based on the image and/or data set information that is observed, the invention provides an interpretive result. The term "interpretive result" is defined herein to mean a diagnosis (or a proposed diagnosis), or a change in physical condition or medical status over time, which a medical practitioner can consult in order to propose a course of treatment for the individual patient in question. It is not to be inferred that the suggested diagnosis or indication of physical condition or medical status is to be taken as medical advice per se, but rather should be understood as an aid to a practitioner, who must still apply his or her best medical judgment in counseling the patient.

Figure 2:
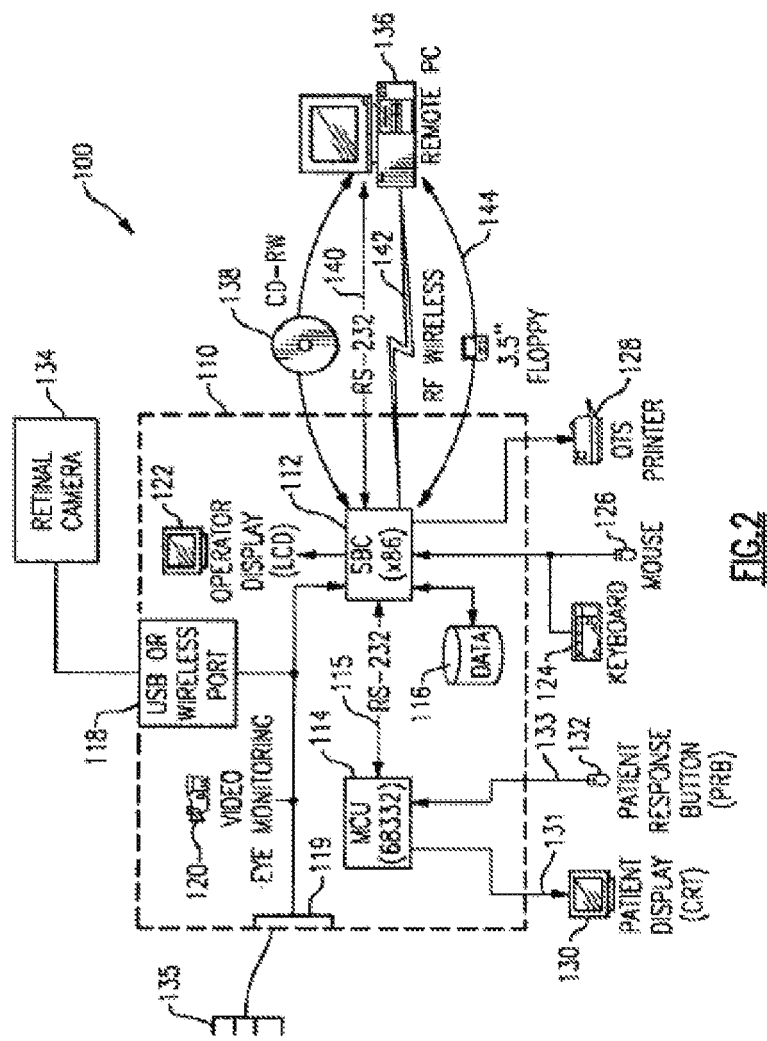
FIG. 2 is a schematic representation of an exemplary apparatus suitable for use according to the invention.

Turning to FIG. 2, there is shown a schematic representation of an exemplary apparatus 100 suitable for use according to principles of the invention. The apparatus 100 comprises a core portion 110 that in some embodiments can be portable or hand held. The core portion 110 comprises a processor 112, which in some embodiments is a single board computer (SBC). The SBC is based on a microprocessor, such as an Intel x86 family member or an equivalent processor. The processor 112 communicates with a microcontroller (MCU) 114 by way of a bus 115, which is in one embodiment an RS-232 bus. In some embodiments the MCU 114 is a Motorola MC68332, which is a highly-integrated 32 bit microcontroller that combines high-performance data manipulation capabilities with peripheral subsystems. The Motorola MC68332 comprises a 32 bit CPU, a system integration module, a time processing unit, a queued serial module and a 2 Kbyte static RAM module with time processing unit emulation capability. A memory device 116 is connected bi-directionally with the processor 112. The memory device can be any conventional machine-readable and -writeable storage device, including any or all of RAM, DRAM, SDRAM, magnetic memory, and optical memory. The core portion 110 also comprises a port 118, such as a universal serial bus (USB) or wireless port, for attaching external devices, such as a retina camera 134, to the core portion 110. In some embodiments, an optional port 119 is provided for attaching one or more electrodes 135, other signal acquisition hardware, to the core portion 110.

The core portion 110 also comprises an eye monitoring device 120 for monitoring an eye of a person being tested or evaluated, including motion of the eye. In FIG. 2, the eye monitoring device 120 is represented by a video camera; however, another embodiment is described hereinbelow, in which a simpler and less expensive device comprising one or more linear charge-coupled device (CCD) arrays is presented. The core portion 110 further comprises a display 122, for displaying information to an operator of the instrument, which display 122 in some embodiments is a liquid crystal display (LCD). Additional portions of the instrument are attached to the core portion 110.

In some embodiments, the core portion 110 is connected to one or more of operator input devices, which in some embodiments are a keyboard 124, a mouse 126, or other devices such as a microphone (not shown). The operator input devices communicate with the processor 112 by way of any conventional wired or wireless connection. In some embodiments, the core portion 110 is connected to one or more output devices such as a printer 128 or a speaker (not shown) for communicating to a user of for creating a hard copy of a record, such as the observations and assessments that are generated during a test. By use of the operator input and output devices, an operator can introduce, and can record as hard copy, information such as a person's name, other identifying information, and other patent-related information such as tonometer intraocular pressure, patient-history, family history, blood pressure, vital signs, medication, and pupillometry, as well as any test conditions, such as an applied stress. An applied stress can comprise any one of intra ocular pressure variation, blood pressure variation, oxygen concentration variation, exercise, flashing light, drug administration, administration of insulin, and administration of glucose, or combinations thereof.

A display 130 is provided for displaying test patterns or other material to a person being tested. The display 130 is connected to the core portion 110 by way of an electrical connector and cable 131 and receives signals from the MCU 114 as input to be displayed. The core portion 110 also has attached thereto a response device 132, such as a mouse or a button that can be manipulated or otherwise activated by a person being tested to communicate responses to the MCU 114 by way of a cable and connector 133. In some embodiments, the display 130 and the response device are a unitary device, such as a touchscreen, and/or the connections with the MCU 114 are made by wireless methods, such as RF or infrared communication links using any conventional wireless technology (for example, 802.11a, 802.11b, or 802.11g).

The core portion 110 is connected to a retina camera 134 by way of the port 118, for viewing the fundus of an eye. In one embodiment, the retina camera 134 is a device such as the Welch Allyn Model 11820 PanOptic.™. Opthalmoscope, available from Welch Allyn, Skaneateles Falls, N.Y., with the addition of a video pickup to provide an electrical input signal to the core portion 110 of the apparatus 100.

In one embodiment, the retinal camera comprises a sensor such as a CCD array that converts detected light into charge signals. The charge signals are in general proportional to an illumination level and a duration of an exposure. The charge signals are converted, on a pixel by pixel basis, into analog signals or digital signals, as may be desired using conventional circuitry, such as switching circuitry, sample and hold circuitry, amplification circuitry, filters, and analog to digital converters. Digital representations of the images detected can be provided with resolution defined by the capability of an analog to digital converter, ranging today from one bit resolution to 24 bit resolution, and with higher resolution as may become possible in the future. Both gray scale and color can be resolved. Additional detailed description of embodiments of video devices suitable for use according to principles of the invention is presented in U.S. Pat. No. 6,527,390 B2 and U.S. Patent Application Publication No. U.S. 2002/0097379 A1, both of which are assigned to the common assignee of this application, and the entire contents of each of which is hereby incorporated herein by reference.

In some embodiments, one or more electrodes 135 can be attached to the core portion 110 by way of a port 119. The one or more electrodes 135, or other signal acquisition hardware, are used to acquire electrical signals, for example, electrical potentials generated during testing, such as visually evoked potentials or other electrical signals useful in detecting responses of a person being tested.

A computer 136, which in various embodiments is a personal computer, a laptop computer, or another general purpose programmable computer of similar or greater capability, is provided for analysis of images and data sets that are collected in the course of testing a person. The images and data sets are communicated from the core portion 110 to the computer 136 by way of any of a wired connection link 140, such as an RS-232 communication bus, a wireless communication link 142, such as RF or infrared, or by transfer using removable media such as a CD-RW disc 138 or a floppy or zip disk 144. In some embodiments, communication from the computer 136 to the core portion 110 is provided by any of the wired link 140, wireless link 142, and transfer using removable media such as CD-RW disc 138 and floppy or zip disk 144, so that commands in the form of programs, program modules, or individual commands to perform a specific action can be downloaded from the computer 136 to the core portion 110, or can be accessed by the core portion 110 while resident at the computer 136. To this end, each of the computer 136 and the core portion 110 are provided with the appropriate ports and/or read-write devices for reading and writing media as necessary. The core portion 110 and the computer 136, as well as the other attached devices, are powered by conventional line voltage connections using wall plugs and power supplies, or by the use of batteries, as appropriate, depending on the intended use of the apparatus, e.g., in an office setting, or in a field setting.

FIGS. 3A-3D show generally an approach to providing an eye monitoring device 120 useful for monitoring the motion of an eye. FIG. 3A shows a schematic diagram 200 of the disposition of an eye monitoring device 120 relative to an eye 260 of a person being tested. In addition, FIG. 3A indicates at a high level the relative disposition of components within the eye monitoring device 120, which is a hand held, portable device in the embodiment depicted. The eye monitoring device 120 comprises, in one embodiment, a handle 210 that provides a griping structure for a practitioner to hold and position the eye monitoring device 120 relative to the eye 260. The handle 210 is adapted to contain the battery useful for operating the device and the electronics useful for manipulating data, providing control signals, and communicating commands and data to and from the eye monitoring device 120. A head portion 220 of the eye monitoring device 120 contains a display 230, such as a CRT, for displaying a test pattern to the eye 260. The head portion 220 additionally contains one or more sensors 240 that are aimed to detect light reflected from a surface of the eye 260. The one or more sensors 240 in one embodiment are 1024.times.1 CCD arrays capable of detecting light at each of 1024 pixel locations, and providing an electrical signal proportional to an intensity of light detected at each pixel. The one or more sensors 240 are focused on a surface of the eye 260 by optics 250, which can be constructed of one or more components made from any convenient optically transmissive material such as glass or plastic.

FIG. 3B shows a diagram 202 that depicts the interrelationship among the features of an eye 260 of a person being tested, and the areas 242, 244 of the eye sensed by two sensors. The eye 260 is being viewed straight on in FIG. 3B, and features of the eye 260 including the white area 262, the iris 264, and the limbus 266 of the iris 264 are represented. Two areas of focus 242, 244 of two sensors, such as the one or more sensor 240 of FIG. 3A, are depicted on the surface of the eye 260. One area of focus 242 is positioned along an imaginary horizontal line (i.e., line 268 in FIG. 3C) passing through the center of substantially circular limbus 266. A second area of focus 244 is positioned along a second imaginary horizontal line parallel to the first imaginary horizontal line, but above (or alternatively, below) the first area of focus 242 by an offset of dimensions of millimeters. Each of the two sensors (not shown) can detect an intensity of light reflected from different locations on the surface of the eye 260. A white portion 262 of the surface of the eye 260 will in general reflect light more strongly than a darker portion of the surface of the eye 260, such as the iris 264, or the pupil of the eye situated within the iris 264. As the eye moves, the change in intensity of light reflected from the white portion 262 as compared to the intensity of light reflected from the iris 264 is tracked. Position is measured as a pixel location counted from one end of a sensor 240. The position of the change in intensity of reflected light corresponds to the location of the limbus 266. When the two sensors detect a change in the position of the limbus, the direction of motion of the eye can be deduced. By applying standard discrete time analysis, the velocity of the motion can also be deduced as x-axis velocity=k(DX/DT), where k is a constant, DX is a change in position along an X axis, and DT is a change in time, and a y-axis velocity can be determined as y axis velocity=k(DY/DT), where DY is a change in position along a Y axis. As is well known in the mathematical analysis arts, two data inputs that are independent with respect to x- and y-axis motion are sufficient to determine both motions and their velocities.

FIG. 3C shows a diagram 204 that depicts the interrelationship between the features of an eye 260 of a person being tested, and the area 242 of the eye sensed by one sensor. In FIG. 3C, the features corresponding to those described with respect to FIG. 3B are indicated by like numerals. In the event that the eye 260 only moves horizontally, the x-axis motion is the only motion that is detected. Accordingly, only one data input that tracks x-axis motion is required, and the area 242 aligned along the centerline 268 of the limbus 266 is sufficient. A procedure useful in constraining the motion of the eye 260 to the horizontal direction is described next.

FIG. 3D shows a diagram 206 that depicts a test pattern 282 and a fixation signal 290 that is useful for fixating an eye 260 of a person being tested when one sensor is employed in the eye monitoring device 120. The CRT 230 of FIG. 3A provides a frame 280 of visually displayed information. A test pattern 282 is disposed within frame 280, comprising one or more vertical lines 284 that can be traversed horizontally over a background 286. The eye 260 of the person being tested will in general attempt to follow the motion of the one or more lines 284. However, there in general can be a wandering of the gaze of the eye 260 in an upward or downward direction while the eye 260 attempts to follow the horizontal motion of the lines 284. The fixation signal 290, which is a prominent solid line segment disposed horizontally across the test pattern 282, within a field of view of substantially 5 degrees total angular height or less, is provided to prompt the eye 260 to fixate vertically along the horizontal line 290 while not interfering with the proclivity of the eye 260 to follow the horizontal motion of the one or more vertical lines 284.

Figure 4:
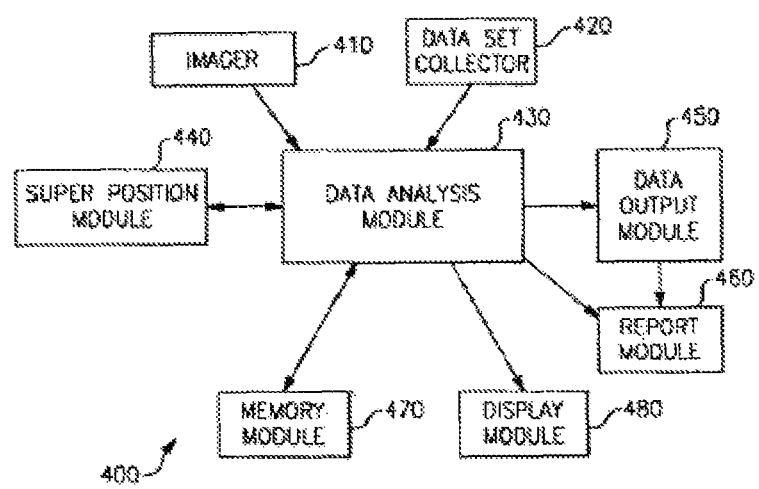
FIG. 4 is a flow chart showing the steps in the operation of the instrument of the invention, or alternatively, showing the interrelationships among the modules comprising apparatus according to the invention.

FIG. 4 is a flow chart 400 showing the steps in the operation of the instrument and method of the invention, or alternatively, showing the interrelationships among the modules comprising apparatus according to the invention. The description will be presented in terms of modules, but those of ordinary skill will also understand the figure as describing the steps of performing the method of the invention. Information is collected by imager 410 and data set collector 420 as necessary. In one embodiment, the information is a plurality of images. In another embodiment, the information is a plurality of data sets. In yet another embodiment, the information comprises at least one image and at least one data set. The information is transferred to the data analysis module 430 for analysis. A memory module 470 in bi-directional communication with the data analysis module 430 can record information sent from the data analysis module 430 in raw form, in analyzed form, or in both forms. Furthermore, the memory module 470 can store information, including as an archival storage, and can provide stored information to the data analysis module 430 as required. For example, the memory module 470 can provide information that was recorded during a previous visit of a patient to a medical practitioner for the purpose of comparing current information observed from the patient with historical information. Archived information can be stored locally or at a remote location. A remote storage capability, which is not shown, can be connected to memory module 470 and or to data analysis module 430 by any convenient means, including wire connection, wireless connection, and by the physical movement of storage media, such as floppy disks, CD-ROM disks, DVD disks, magnetic tape, memory cards, and similar moveable storage media.

A superposition module 440 is in bi-direction communication with the data analysis module 430. Information can be sent from the data analysis module 430 to the superposition module 440, and data that has been subjected to superposition can be sent from the superposition module 440 to the data analysis module 430. As described below with respect to FIG. 5, the superposition module 440 in some embodiments comprises a plurality of other modules.

The data analysis module 430 is in communication with a data output module 450, which can provide information to a user. The data analysis module 430 is optionally in communication with a report module 460, which can provide reports to a user. The data analysis module 430 is optionally in communication with a display module 480 that can display images, sets of data, and superpositions of information to a user for visual examination of the information.

Figure 5:
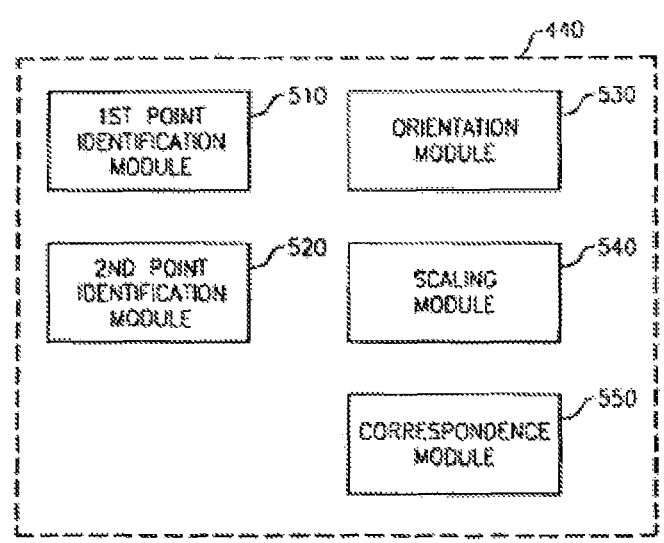
FIG. 5 is a diagram that shows components of a superposition module according to the invention.

FIG. 5 is a diagram 500 depicting components of a superposition module 440 according to the invention. The superposition module 440 can optionally comprise first and second identification modules 510, 520 that identify first and second fiduciary points in an image or a data set. In some embodiments, the first and second identification modules 510, 520 are the same module. The superposition module 440 also optionally comprises an orientation module 530, a scaling module 540, and a correspondence module 550. The orientation module 530 orients images or data sets to be superimposed about a fiduciary point so that a first metric and a second metric are oriented in selected orientations. The scaling module 540 scales an image or data set so that a first unit of measure associated with the first metric and a second unit of measure associated with the second metric in each image or data set to be superimposed are substantially equal to selected first and second values. The correspondence module 550 creates a one-to-one correspondence between the fiduciary point, the first metric and the second metric in a first image or data set to be superimposed with the fiduciary point, the first metric and the second metric in a second image or data set to be superimposed.

In some embodiments, the first metric and the second metric are first and second axial directions. In one embodiment, the first and second axial directions are coplanar but not parallel axial directions, such as two axes, for example the x and y axes in a Cartesian coordinate system. Other coordinate systems can be used equally well. In such an embodiment, the first unit of measure associated with the first metric is a length along the first axial direction, such as a number of units along an x-direction, and the second unit of measure associated with the second metric is a length along the second axial direction, such as a number of units along a y-direction. In other embodiments, the first metric is a first axial direction, the second metric is an angular displacement from the first axial direction, the first unit of measure associated with the first metric is a length along the first axial direction, and the second unit of measure associated with the second metric is a unit of angular measure. For example, the first metric is a heading or compass direction that is considered to be zero degrees relative to an origin (i.e., due North on a map), and the first unit of measure is a geometric distance along the heading (i.e., a radius of a circular arc), the second metric is an angle (i.e., $\theta$ degrees clockwise rotation), and the second unit of measure is an angular value, such as $\theta=90$ degrees. When a plurality of images, a plurality of data sets, or at least one image and at least one data set are scaled, rotated and/or translated such that corresponding first and second metrics are made to coincide, the plurality of images, the plurality of data sets, or the at least one image and at least one data set will be capable of being superimposed.

In the display of such images, one can present the images side by side, or in superimposed configuration, one upon the other. The images can be compared by simple superposition, to show interrelationship of one or more features that appear in each. Alternatively, by superimposing one image on the "negative" of another, it is possible to make the difference (or the change between a first image and a second image) readily apparent. For example, a new feature appearing in a later image will become the only feature (or a highlighted image) displayed in a display comprising a "negative" of a first image superimposed upon (or summed with) a second, later, image. Images can be displayed in false color as well, so that regions of data sets that comprise substantially similar values can be readily discerned. For example, an image in which a first color is used to represent data points below a threshold value and a second color is used to represent data points exceeding the threshold value provides a display for a viewer in which the regions having specified ranges of values are readily identified. As required, more than two ranges can be assigned, and corresponding different colors can be used in the display of the data set.

Figure 6:
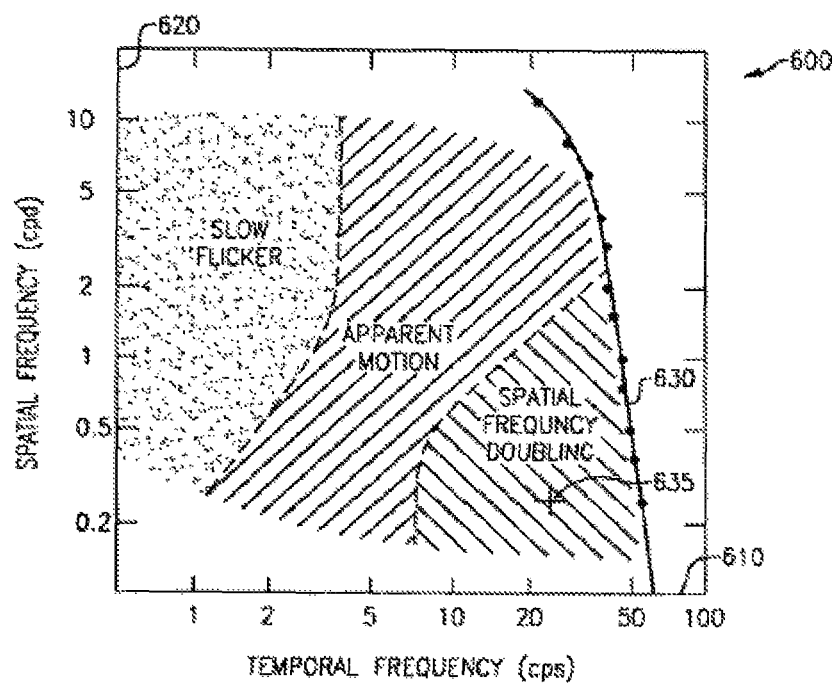
FIG. 6 is a diagram showing a region of frequency space having both temporal and spatial frequency variations, and indicating a typical person's reaction thereto, as is known in the prior art.

FIG. 6 is a diagram 600 showing a region of frequency space having both temporal and spatial frequency variations, and indicating a typical person's reaction thereto, as is known in the prior art. FIG. 6 is based on observations made by D. H. Kelly, which results were reported some years ago. In FIG. 6, the horizontal axis 610 is a logarithmic axis that represents the temporal frequency in cycles per second (cps) ranging from close to zero to approximately 100 cps. In FIG. 6, the vertical axis 620 is a logarithmic axis that represents the spatial frequency in cycles per degree (cpd) ranging from close to zero to approximately 20 cpd. In this circumstance, degrees are measured as angular measure on the retina of an eye. As can be seen, there is a region 630 extending from about 7 cps to about 60 cps and from about 0.1 cpd to about 2 cpd, which region 630 is labeled "Spatial Frequency Doubling." The region 630 further includes a point indicated by the cross 635 that is in some embodiments a target spatial and temporal frequency operating point in the vicinity of 25 cps and 0.3 cpd. Within the Spatial Frequency Doubling region 630, a person with normal vision see a pattern that appears to be doubled in spatial frequency from its actual spatial frequency. Persons with compromised vision, or with other neurological difficulties, have difficulty perceiving the doubled spatial frequency pattern, or see it only at higher contrast.

Figure 7B:
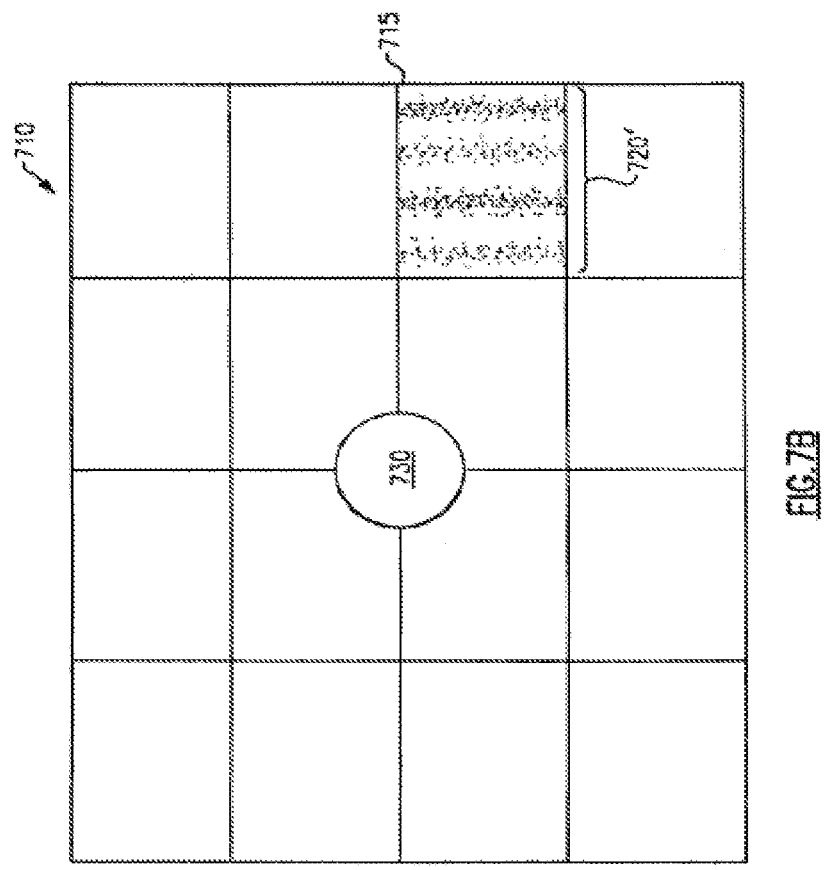

FIGS. 7A and 7B are drawings that depict a display space 710 that is segmented and includes an illustrative contrast pattern 720. In FIGS. 7A and 7B, one segment 715 includes a high contrast pattern 720 and one segment 715 includes a lower contrast pattern 720', respectively. Each of FIGS. 7A and 7B include a central region 730 that can in some embodiments be used to locate a fixation element, or a different contrast pattern than the patterns shown in segment 715. As may be understood from comparison of FIGS. 7A and 7B, the more strongly contrasting pattern 720 of FIG. 7A can be transformed into the low contrast pattern of FIG. 7B by decreasing the dynamic excursion (or dynamic range) of the signal comprising high contrast pattern 720. High contrast pattern 720 is generated by providing a sinusoidally varying signal having bright and dim extremes, or strongly illuminated regions and weakly illuminated regions. It is expected that those with compromised neurological condition will perceive the contrast signal to disappear at a higher contrast level threshold than those with normal vision and normal neurological conditions. Dyslexia may be indicated by an inappropriate response to contrast sensitivity tests, because in dyslexia the eye and the brain collaboratively misinterpret the spatial relationships in data.

Figure 8A:
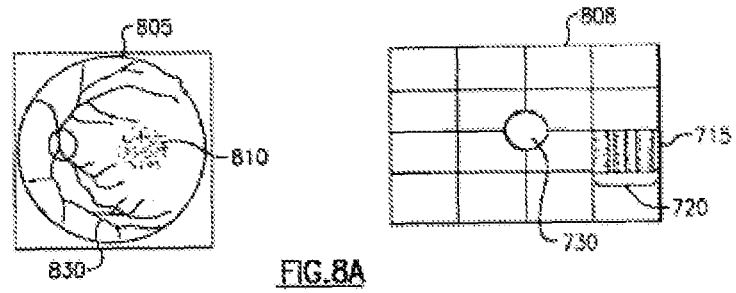
FIGS. 8A, 8B and 8C are diagrams that show the relationship between an image and a data set, two images taken at different times, and a series of images, false color data representations, and data sets, respectively, according to principles of the invention.
Figure 8B:
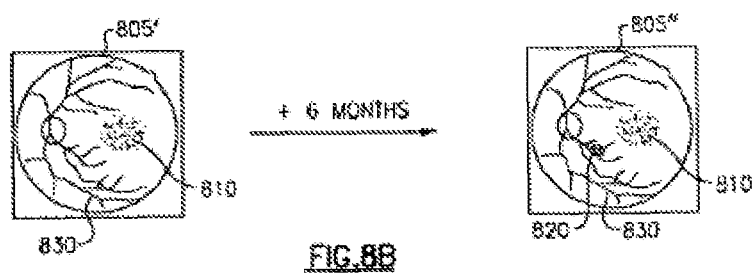
Figure 8C:
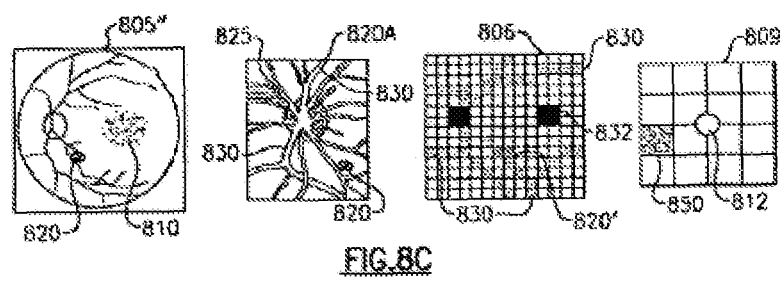

FIGS. 8A, 8B and 8C are diagrams that show the relationship between an image and a data set, two images taken at different times, and a series of images, false color data representations, and data sets, respectively. As depicted in FIGS. 8A, 8B and 8C, the interrelated images and data sets are displayed side-by-side. It will be understood, perhaps most readily by considering the two images of FIG. 8B, that two or more pieces of information can also be superimposed. Careful comparison of the leftmost image of FIG. 8A with either of the images of FIG. 8B will show that the leftmost image of FIG. 8A is larger in size than either image of FIG. 8B. As is seen in the images of FIG. 8B, many features of one image are also present in the other image, and the two images could easily be presented as either the superposition of one on the other, or the superposition of one over the negative image of the other, thereby highlighting the differences between the two images. In one embodiment, viewing the information in side-by-side presentation makes it easier to compare information, and may allow certain forms of analysis, but requires the viewer to synthesize the data to find certain correspondences. In other embodiments that use superposition, benefits that accrue include the ability to highlight, the ability to subtract or otherwise process information, and the ability to assure that two pieces of information are representative of the same area or feature.

In FIG. 8A, the left image is an image 805 of a retina of an eye, including a macula 810 near the center of the image. In FIG. 8A, the right image 808 is a map of a contrast level observation, in which the central region 730 corresponds to the macula 810, and the region 715 having the contrast pattern 720 therein is intended to convey the information that the observed response of the eye was acceptable in that region 715.

In FIG. 8B, the left image 805' is a first image of a retina of an eye, in which the macula 810 is again visible. The right image is an image that represents a second image of the same retina taken 6 months later, in which the macula 810 is again visible. However, in the later right image 805", a new feature 820 appears to the left of the macula 810. The side-by-side presentation in FIG. 8B is intended to show that for highly similar images, it is relatively easy to compare two or more images, as can be seen in a comparison of the two images in FIG. 8B, wherein a large number of features can be observed to be substantially common to both images, such as the position and shape of imaged blood vessels 830. While the new feature 820 is readily apparent, it is not clear from the image whether the new feature 820 represents an active proliferation of capillaries (i.e., blood is still circulating in blood vessels) or whether the new feature is a blood clot that has long since ceased to circulate. More information is available from a consideration of the images shown in FIG. 8C.

FIG. 8C comprises four pieces of information. The leftmost image is the image 805" as seen in FIG. 8B, right side. This is a high resolution image that is displayed on a pixel by pixel basis, wherein much detail is available for analysis. Again, the feature 820 is visible. The next panel in FIG. 8C (i.e., the second image from the left) is a false color oxygen saturation view 820A of the region of the retina in the vicinity of the new feature 820. In the second image 820A, one can discern that the new feature 820 is a region centered on a junction 825 of blood vessels 830, which gives further credence to the analysis that the feature 820 represents blood high in oxygen. The next image 806 (i.e., the third image from the left) is a false color thermal image taken at lower resolution that the second image from the left (i.e., 4 by 4 pixels rather than one-by one pixel), which image shows the new feature 820, for example, as a red (false color) square region 820' at the junction 825 of a yellow (false color) blood vessels 830. The red false color is representative of a higher temperature than the immediate surroundings, suggesting that the new feature 820 is a proliferation of capillaries that comprises fresh, warm blood, rather than an old bleed which would have reached the same background temperature as the surrounding tissue, and therefore would have been represented by the same color (green). A second red false color region 832 is also shown in the false color image, the second red false color region corresponding to the macula 830, which is rich in blood vessels, and therefore would be expected to be somewhat warmer than the surrounding area. The rightmost panel of FIG. 8C is a representation 809 of a data set obtained from a contrast sensitivity measurement, in which the central region 812 corresponds to the macula 810 of the leftmost image 805". The data set is represented at a rather low resolution as compared to the leftmost image 805", for example using a 10 pixel by 10 pixel resolution. The gray region 850 of the contrast sensitivity data set represents a region of severely degraded response, which corresponds to the location of the new feature 820 in the leftmost panel of FIG. 8C. One can then recognize from the aggregation or interrelation of images 805", 820A, 806, and 809, that the new feature 820 gives all the indications of a region representing an active capillary structure, the structure negatively impacting the vision of the eye under consideration.

Figure 9:
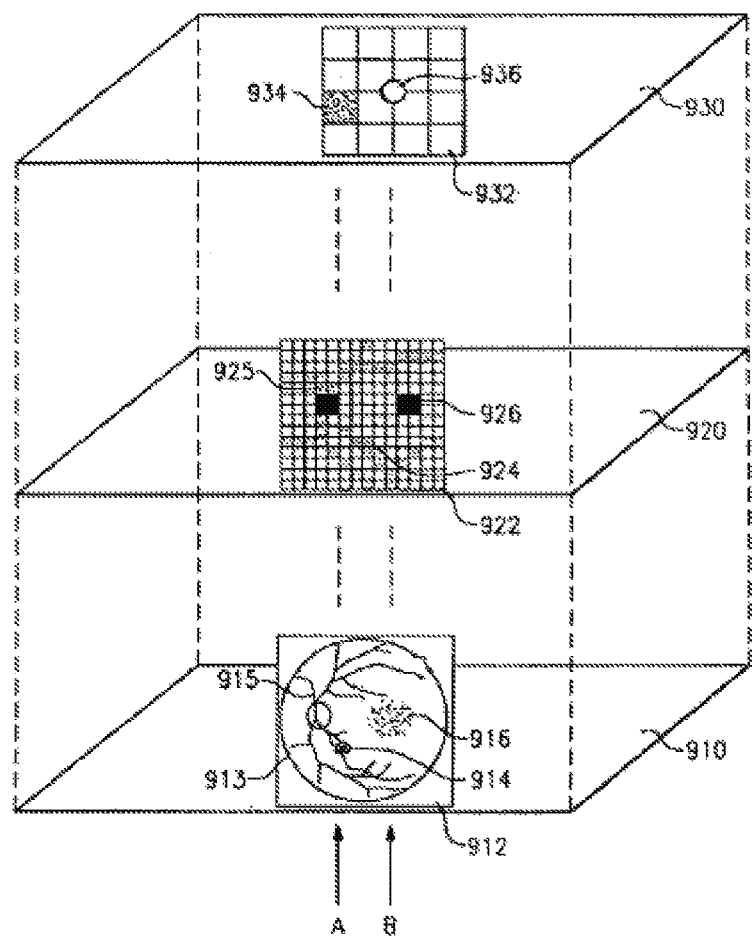
FIG. 9 is a schematic showing the relationship among superimposed images and/or data sets, according to principles of the invention.

FIG. 9 is an illustrative schematic in exploded form showing the relationship among superimposed images and/or data sets. In FIG. 9 there are three parallel planes 910, 920 and 930. Situated on each plane is an image or a map of a data set. For example, there appears on plane 910 image 912 that is a photographic image of the fundus of an eye such as is captured by a retinal camera 134. Along axis A, which is denoted by a dotted line extending between the planes 910, 920, 930, there is in image 912 a spot 914, which corresponds to the area of capillaries described as the new feature 820 of FIGS. 8B-8C. Along axis B, which is also denoted by a dotted line extending between the planes 910, 920, 930, there is in image 912 a macula 916, which corresponds to the macula of FIGS. 8A-8C. There are blood vessels 913 that have a junction 915, as well as other features visible in image 912.

In plane 920 of FIG. 9 there appears an image that is a false color thermal image taken at a lower resolution than the second image from the left (e.g., 4 by 4 pixels rather than one-by one pixel), which image shows the new feature 820 as a red (false color) rectangular region 924 at the junction 925 of yellow (false color) blood vessels 923. The A axis passes through the rectangular region 924 representing the false color image of the new feature 820. The B axis passes through the square false color region 926 corresponding to the macula 916 of the eye.

In plane 930 of FIG. 9 there appears a map 932 corresponding to a data set recorded as a result of a contrast sensitivity test. In the map 932 there is a fixation pattern 936 which is the area upon which the gaze of the eye under test is expected to fall, and as described above, is a location where the gaze of the eye can be observed to fall by instrumentation of the invention. Accordingly, the fixation pattern 936, or a selected pixel of the fixation pattern 936, such as the center of the fixation pattern 936, can be placed along Axis B so as to coincide with (or to be superimposed upon) the image of the macula 916 and the false color image 926 of the macula. Also, the region 934 of the map 932 corresponding to the data set obtained in the contrast sensitivity test indicates a diminution in the ability of the eye to perceive the contrast pattern, which diminution is denoted by a gray hue in area 934. In some embodiments, the depth or intensity of the gray hue, or the use of a range of false colors, can be used to represent the severity of the diminution of perception. The region 934 is aligned with Axis A, corresponding to the area of the retina having the new feature 820 that is depicted as region 914 of the fundus photograph 912. As needed, the sizes of one or more of the various images and maps or other representations of data sets can be expanded or contracted so that superposition is possible. Furthermore, any of the images or representations of data sets can be translated and/or rotated to orient one with respect to another so that superposition can be accomplished. As is understood in the geometric arts, superposition can be attained by superimposing two selected points in a first image with the corresponding two selected points in a second image. Superposition can also be attained by defining a pair of coplanar but not parallel vectors in each image, causing the dimensions of the images to be commensurate by expanding or contracting at least one image as needed, and aligning the vectors. Superposition can also be accomplished by defining an origin and a vector in each image, causing the dimensions of the images to be commensurate by expanding or contracting at least one image as needed, and aligning the origins and the vectors.

Figure 10:
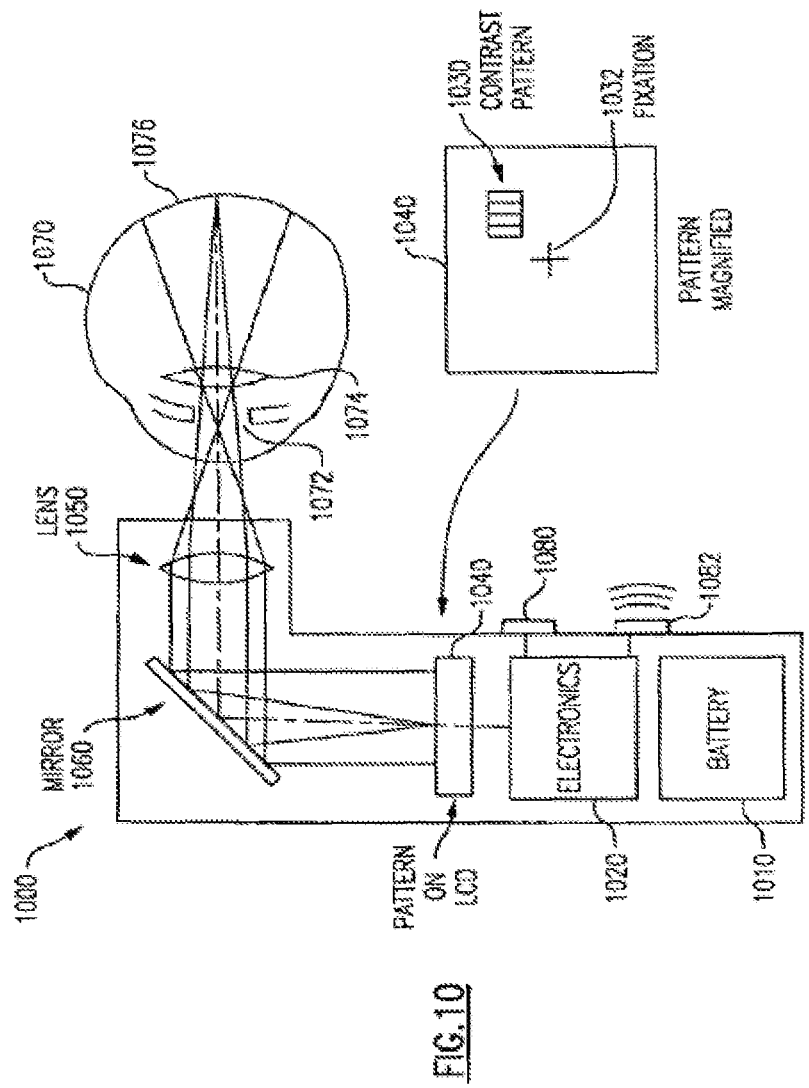
FIG. 10 shows a hand-held apparatus that measures a person's visual contrast sensitivity according to principles of the invention.

According to principles of the invention, it is possible to determine blood glucose by measuring the eye of a patient using an instrument as shown in FIG. 10, and described in more detail below.

The operation of the instrument is based on the observation that in humans, and perhaps in other animals, the retina of the eye has one of the fastest metabolic rates in the body. Diabetes is a disease that is characterized by poor control of blood glucose. Diabetics attempt to control their blood glucose levels by balancing food intake, exercise and medication, such as insulin or other medications. In order to determine whether and how much insulin to administer, the blood glucose level of the individual must be measured. Today, diabetics can be required to draw blood, commonly by pricking a finger, several times a day. The procedure of drawing blood can be painful and invasive, and compliance with a strict medical regimen may be affected in a negative way.

The blood glucose determination apparatus of the invention, and its method of use, may have applicability in blood glucose monitoring in diabetics, with several advantages. First, the measurement does not require the drawing of blood, and is therefore painless. In addition, the measurement device will not require the use of consumables, such as chemicals or treated strips that interact with drawn bodily fluids. The lack of consumables, other than a replaceable battery, will reduce the operating cost per test, making testing possible at lower operating costs than in conventional tests that require interaction of a bodily fluid with a test medium. In addition, the absence of consumables will make testing more convenient in that the user does not need to remember to transport consumable items when he or she travels from home, even during the day. Another benefit is the fact that the test will be relatively unobtrusive and not embarrassing, so that it can be performed quickly and in public settings as may be required.

Experimenters have studied the effects of glucose on the retina, the heart, and the kidneys for many years. These organs are well-known to be negatively affected in persons suffering from diabetes. One relation that has been noted is the ability of the retina to observe or determine contrast, which varies with the blood glucose level. In particular, a relation between a person's visual contrast sensitivity and the person's blood glucose level may provide a basis for measuring the blood glucose level. It may be necessary or advantageous to calibrate the measurement by the use of a blood glucose measurement using drawn blood. However, once the calibration is performed, the necessity to draw blood to make actual measurements is obviated. The calibration might also be performed by using different blood glucose levels, e.g., high blood glucose, normal blood glucose, and low blood glucose, which levels may be induced by deliberate administration of foodstuffs or by the deliberate withholding of food and having the person to be tested perform exercise.

The apparatus 1000 of FIG. 10 is in one embodiment a hand-held device that measures a person's visual contrast sensitivity in the same way that the FDT device measures contrast sensitivity in persons exhibiting glaucoma and/or other neurological disorders. As shown in FIG. 10, the apparatus 1000 comprises a power supply 1010 such as a battery and electronics 1020 for generating and displaying a contrast pattern 1030 that appears on a display 1040 and for computing a result of a blood glucose measurement. In one embodiment, the electronics 1020 comprises a microprocessor or microcontroller and memory, as well as the necessary signal acquisition and conditioning hardware for responding to commands from the user, as well as software that may be recorded in nonvolatile form in a machine-readable medium. In one embodiment, the display 1040 will be an LCD similar to those used in present-day camcorders. In other embodiments, other display technology may be used. The apparatus 1000 also comprises a lens 1050 for focusing an image of the contrast pattern 1030 so that the image may be viewed by an eye 1070 of a user. The contrast pattern 1030 can also include a fixation element 1032, for assisting the user in fixing his or her gaze on a particular location of the display. The apparatus 1000 also can comprise an optical element 1060 useful for changing a size of the image and/or for causing the light from the image to be correctly oriented for the user to view the image. In some embodiments, the optical element 1060 is a mirror, which can be a planar mirror, a convex mirror, or a concave mirror as required. The eye 1070 as shown comprises an iris 1072 and a lens 1074, as is commonly found in eyes for causing an image to fall on a retina 1076 of the eye.

In use, the user holds the apparatus 1000 in a position such that the user can observe the contrast pattern 1030 and the fixation element 1032. The fixation element 1032 help to insure that the contrast pattern 1030 will fall on the same portion of the user's eye 1070, such that the same area of the retina 1076 of the eye 1070 is interrogated. The area can be any area of the retina that represents the test subject's reaction to blood glucose level or concentration. In some embodiments, the area is the macula of the eye 1070, in which case the contrast pattern 1030 and the fixation element 1032 are coincident. For example, the contrast pattern 1030 can be centered on the fixation element 1032. In one embodiment, the user can activate a button 1080 on the apparatus 1000 during a time when he or she can see the contrast pattern 1030. The button 1080 is connected electrically to the electronics 1020. In one embodiment, the user releases the button 1080 to indicate that the user can no longer distinguish the contrast sensitivity pattern 1030, thereby completing a test cycle. The contrast sensitivity pattern 1030 first appears with dark lines and light lines, which respectively become lighter and darker with time. At some point, either when the two sets of lines in the contrast sensitivity pattern 1030 have the same optical characteristic and cease to be distinguishable, or when the user is no longer able to distinguish between the light and dark sets of lines, the user would be expected to release the button 1080. After the electronics 1020 processes the data it receives, and computes a blood glucose level for the user, the result may in some embodiments be displayed to the user by being presented on the display 1040 of the apparatus 1000 in any of an alphanumeric format, a pictorial format (i.e., a graphic or an icon), an audible signal provided by a speaker 1082, a tactile signal provided by a vibrator, or any combination of signals. In alternative embodiments, the result can be transferred, for example by wireless communication, to another device, such as a personal digital assistant, a cellular telephone, a computer, a data recorder, a printer, or an external display. For example, a person may wish to have a result that indicates a serious abnormality, such as severe hypoglycemia, reported to another trusted party to make sure that appropriate medical intervention takes place.

In a further embodiment, the apparatus additionally comprises an analysis module comprising a programmable processor and computer software recorded on a computer-readable medium. The computer software (or alternatively "software"), when operating, performs a plurality of steps. The software controls the operation of the apparatus generally, including controlling input and output functions of the apparatus, such as receiving commands and data from a user of the apparatus to cause the apparatus to perform its operations, and providing to the user of the apparatus information, such as information relating to the outcome of one or more analyses, information describing the condition of the apparatus, and prompts or other information that indicates that the user may provide additional information about the person being tested so as to improve the outcome of the analysis performed by the apparatus. As regards the detailed operation of the software, in one embodiment the software interrelates at least two disparate kinds of information selected from one or more images and one or more data sets to attempt to obtain an interpretive result relating to the condition of the person. In the event that the attempt to obtain an interpretive result relating to the condition of the person provides a result representing a state of normal health, the software controls the recording the result and terminating the analysis.

In the event that the attempt to obtain an interpretive result relating to the condition of the person provides a result representing a state of health that is not normal health, the software operates to attempt to distinguish a condition represented by the state of health that is not normal health. In the event that the attempt to distinguish the condition represented by the state of health that is not normal health is successful, the software operates to report an interpretive result of the condition, operates to record information for later use, and terminates the analysis.

In the event that the attempt to distinguish the condition represented by the state of health that is not normal health is unsuccessful, the software can additionally report the failure to distinguish a condition. Optionally, the software can additionally prompt a user of the apparatus to provide additional information about the person. Optionally, the software can prompt a user of the apparatus that additional testing can be performed.

The software can additionally operate to iteratively repeat the interrelating step and, as appropriate, each of the conditional steps using the additional information provided in response to the prompt in addition to the at least two disparate kinds of information selected from one or more images and one or more data sets to attempt to obtain an interpretive result relating to the condition of the person. Any specific step can be omitted in an iteration cycle if it appears that the step is unnecessary. The iteration can continue until any of the following conditions occurs, and in general, will terminate when the first of the following conditions does occur: after reporting an interpretive result; operating until an iteratively repeating step is performed a predetermined number of times without distinguishing a condition represented by a state of health that is not normal health; operating until an iteratively repeating step is performed until a specified period of time elapses without distinguishing a condition represented by a state of health that is not normal health; and operating until a user of the apparatus determines that the analysis should be terminated, and intervenes to terminate the analysis.

The disease referred to as ALS is also known as amyotrophic lateral sclerosis (or Lou Gehrig's disease).

Figure 11:
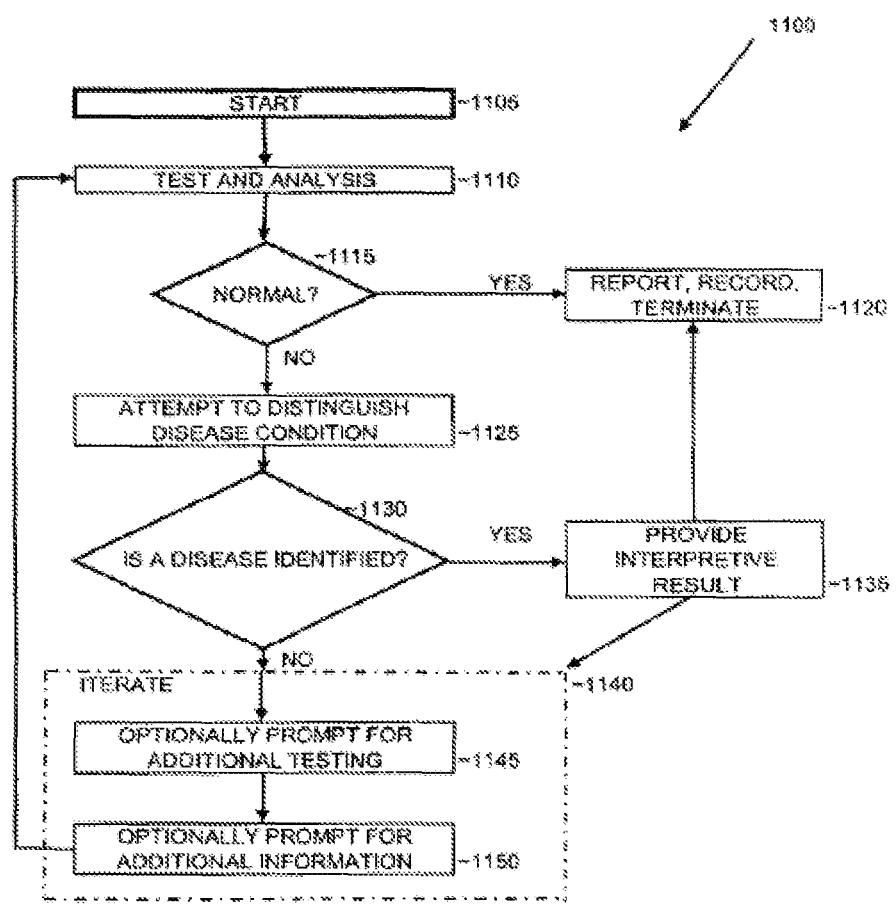
FIG. 11 is a flow chart showing the steps in a measurement process, according to principles of the invention.

FIG. 11 is a flow chart 1100 showing the steps in a measurement process. The process described by the flow chart begins with initialization of the computer system and the software operating on it, including the usual internal checks for proper operation, and initialization of all parameters to default values that the instrument requires for operation, which parameter values in some embodiments are retrieved from a memory accessible by the computer. In some embodiments, a user of the instrument can change the default values in order to perform tests and analysis.

The box 1105 labeled "Start" is intended to represent all of the conventional start-up and "housekeeping" processes that take place when a computerized system is initialized, and can include such events as retrieval of information from a computer accessible memory, a user entering information that identifies the user as a person authorized to operate the system, entry by a user of information that identifies the person who is to be tested, entry of values to replace default values, entry of the time and date (which in some embodiments may be automatically entered), entry of information about the person being tested (for example, vital signs information and/or some or all of a patient history), and entry or retrieval from a memory of other information such as billing or insurance information.

When the computer software is operating on the programmable computer, it can cause the following steps to be performed. In some embodiments, the computer and software are used in obtaining one or both of images (for example, images of an eye or parts thereof) and data sets (for example, data relating to the response of the person to various stimuli). As part of a test, indicated at box 1110, the software can interrelate at least two disparate kinds of information selected from one or more images and one or more data sets to attempt to obtain an interpretive result relating to the condition of the person. The computer and software analyze the interrelated information (images, data and other information).

As indicated at diamond 1115, the analysis attempts to determine whether the images, data and other information are consistent with a normal state of health or are consistent with a state of health that differs from a normal state of health, and to obtain an interpretive result based on the analysis. In the event that the attempt to obtain an interpretive result relating to the condition of the person provides a result representing a state of normal health, corresponding to the arrow labeled "YES" leaving diamond 1115, the software causes the interpretive result to be recorded, and optionally reported, and the test is terminated, as indicated by box 1120.

In the event that the attempt to obtain an interpretive result relating to the condition of the person provides a result representing a state of health that is not normal health, the process follows the arrow labeled "NO" leaving diamond 1115, and the process continues as indicated at box 1125, representing an attempt by the operating software to distinguish a condition represented by the state of health that is not normal health.

At diamond 1130, the software determines whether there has occurred a successful analysis that distinguishes a particular state of health that is not normal health (e.g., a specific disease condition is indicated by the information). In the event that the attempt to distinguish the condition represented by the state of health that is not normal health is successful, the process proceeds according to the arrow labeled "YES leaving diamond 1130, and the software provides an interpretive result of the condition. If the software indicates that the confidence level of the analysis is high enough, the analysis can be terminated, as indicated at box 1120.

However, if the software either does not identify a specific condition that is consistent with the information that has been analyzed, or if the confidence level associated with the analysis is less than some predetermined value, for example 75% confidence that the condition identified is correct, the process can continue according to the arrow labeled "NO" leaving diamond 1130. As will be understood, the user can be signaled that the outcome of the analysis is either indeterminate or of low confidence by either of two possible methods. One method is simply to fail to provide an interpretive result. The second method is to report the failure to distinguish a condition.

The software can cause the apparatus optionally to prompt a user of the apparatus that additional tests can be performed, as indicated at box 1145. The software can cause the apparatus optionally to prompt a user of the apparatus to provide additional information about the person, as indicated at box 1150. Using the additional information, and/or the results of additional tests that generate additional images and/or data sets, the software can again perform analysis as indicated at box 1110, and subsequent steps as indicated above.

As indicated by the box 1140 shown in broken outline and labeled ITERATE, the software can cause the iterative repetition of the analysis to provide an interpretive result. The iterative repetition can continue until the first to occur of: the analysis is terminated according to step 1120; the iteratively repeating step is performed a predetermined number of times without distinguishing the condition represented by the state of health that is not normal health; the iteratively repeating step is performed until a specified period of time elapses without distinguishing the condition represented by the state of health that is not normal health; and a user of the apparatus determines that the analysis should be terminated, and intervenes to terminate the analysis.

Additional tests 1145 and addition information 1150 about a person comprises any one or more of: collecting an additional image; collection of an additional data set; additional information from a magnetic resonance imaging (MRI) test, which can be a structural MRI test or a functional MRI test; patient history data, vital signs data, additional information from a positron emission tomography (PET) test which can be an FDG-PET glucose determination or a C-PK11195-PET test, additional information from a brain biopsy, and additional information from a cognitive impairment test. The order of performing the steps of obtaining an image, obtaining a data set indicative of a neurological disorder, and obtaining said additional information about said person is not critical, and may be performed in any order that is convenient.

Sequential testing can be performed on a person to identify a disease condition that may exist. The person is tested first with the overall screening test to establish if he or she is normal or abnormal (e.g., having one or more diseases, but the exact identity of the disease that may be present is not known prior to testing). If the person is normal according to the screening test, the data observed can be recorded for use as a baseline at a later time, and the testing terminates. However, if it appears that an abnormality (which is taken to be indicative of a disease condition) exists, the person would be tested a second time with a different test more specific to one of the diseases that the instrument embodying the invention can distinguish. In the further testing, the apparatus uses a modified test, which can include one or more changes in spatial frequency, temporal frequency, magnitude or size of stimuli, location of stimuli, color, and contrast. The further testing test has each of those parameters optimized so as to attempt to identify the presence of one of the diseases and not the others. If the person appears to be normal based on the second test, then a third test can be performed with a different set of parameters. Additional information can also be used in performing an analysis of the results of a test, so as to provide an interpretive result. It is possible to iteratively repeat the testing until there is an identification of one or more diseases the person appears to have (since it is possible to have both glaucoma and AD as an example).

In some embodiments, the apparatus for obtaining an interpretive result relating to a condition of a person is used in commercial activity, and financial compensation is received for performing a selected one of displaying the interpretive result and reporting the interpretive result. In some instances, financial compensation is received for performing the testing.

In some embodiments, the apparatus for obtaining an interpretive result relating to a condition of a person is used is a manner wherein the interpretive result comprises an indication of a tendency to develop a disease condition.

In some embodiments, the apparatus for obtaining an interpretive result relating to a condition of a person comprises software recorded on a machine readable medium. In some embodiments, the software when operating repeats its operation for data relating to a second eye of the person to determine a condition of health of the person. In some embodiments, the condition of health of the person obtained from data from one of the first eye of the person and the second eye of the person is used as a baseline condition for testing of the other of the first eye of the person and the second eye of the person. In some embodiments, the condition of health of the person is obtained from data relating to both the first eye of the person and the second eye of the person.

As used in the present application, the term "venue" in any of its variant forms is intended to be interpreted broadly and to include, for example, medical office settings, field test settings (e.g., testing as part of an emergency response at a field location), other settings such as the lobby of a building where screening of individuals for various medical conditions, such as high blood pressure, are from time to time performed, settings such as mobile testing facilities (e.g., medical trailers used for screening persons in a selected geographical area), and commercial testing facilities, such as imaging centers of the type that perform medical imaging.

Optical neuroma is one or more cancers that affect an optic nerve.

Stroke is a form of head trauma. A second form of head trauma is a blow to, or severe shaking of, the head. It can in some instances be localized on one side of the brain or in a specific region of the brain. Stroke can involve either or both of a loss of blood circulation in at least a portion of the brain that can result in death of tissue (for example, caused by a blockage in a blood vessel, such as a blood clot that occludes the vessel) or a leakage of blood from a blood vessel that can cause problems both from lack of oxygen in portions of the brain that loose circulation and from added fluid volume and pressure in the vicinity of the leakage (for example, resulting from a rupture in a blood vessel caused by elevated blood pressure or by loss of elasticity of the blood vessel, or both).

Tests and their analysis can provide information about the site and the cause of loss of neurological function, such as which side or where within the brain a loss occurs, whether the loss is localized in an eye (such as damage to a retina or cells within the eye), or whether a loss occurs in the nerves between the eye and the brain, or whether a loss occurs in the brain.

With regard to the outcome of an analysis, it is expected that there can occur situations in which the result of the analysis is consistent with a first possible state of health that is not normal health with a first probability, and the result of the analysis is also consistent with a second possible state of health that is not normal health with a second probability. If the difference between the first probability and the second probability is not sufficient large to make a clear differentiation between the first and second states of health that are not normal health, the apparatus can provide a report indicating that the first condition is likely to the extent of a first percentage, and the second condition is likely to the extent of a second percentage. The apparatus can optionally prompt the user of the apparatus to provide additional information about the person being tested. In some embodiments, the apparatus can iteratively repeat analyses using the additional information to refine the likelihood that the first condition, the second condition, or other conditions different from a state of normal health are consistent with the images, data and other information that may have been utilized in the analysis. The apparatus can report the results of its analysis, as an interpretive result, and not as a medical diagnosis, to a user thereof. The operation of the apparatus can terminate under any of several conditions, such as after reporting an interpretive result; operating until an iteratively repeating step is performed a predetermined number of times without distinguishing a condition represented by a state of health that is not normal health; operating until an iteratively repeating step is performed until a specified period of time elapses without distinguishing a condition represented by a state of health that is not normal health; and operating until a user of the apparatus determines that the analysis should be terminated, and intervenes to terminate the analysis.

The term "a user of said apparatus" will often refer to a human operator of the apparatus, but can also refer to a machine or system that terminates operation of the apparatus automatically, including upon detection of a fault condition, such as a condition that could cause harm to a person, or upon detection of a condition where an unauthorized person is attempting to access patient information resident in the apparatus, for example in contravention of regulations such as the Health Insurance Portability and Accountability Act of 1996 (hereinafter "HIPAA"). In addition, a user of the apparatus can in some embodiments be a medical data collection and/or recording system.

In some embodiments, the order of obtaining an image, obtaining a data set indicative of a neurological disorder, and obtaining said additional information about said person is not critical, and may be performed in any order that is convenient. For example, patient history and vital signs information may be collected before a person is tested with the apparatus of the invention. Data from other testing methods, such as PET, MRI, and cognitive impairment tests, may be obtained from tests performed before or after the testing of a person with the apparatus. Where there is no requirement that a specified order of steps be adhered to, the present invention contemplates that the steps may be performed in any order, and even with intervening periods of delay, such as the time needed for a person to move from one apparatus to another and for the tests to be scheduled and performed, which apparata may be in different facilities or locations (such as an MRI imaging center separate from a venue where the apparatus of the invention is situated).

A Discussion of Alzheimers Disease

From a neurological perspective, the eye is a part of the brain. The eye does signal processing within the retina and has neurons that attach directly to the brain.

Figure 12:
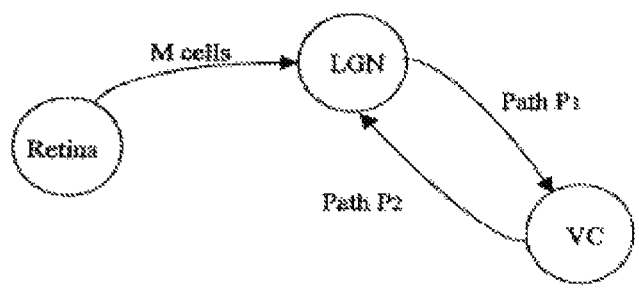
FIG. 12 is a diagram showing the feedback loop associated with the retina, the LGN and the VC.

Ganglion cells lead from the retina to the lateral geniculate nucleus (LGN), which for the purpose of explanation will be called pathway #1 (M). Pathway #2 (P!) leads from the LGN to the Visual Cortex (VC). Pathway #3 (P2) is a feedback loop from the VC back to the LGN. FIG. 12 is a diagram showing the feedback loop associated with the retina, the LGN and the VC.

In glaucoma, the ganglion cells are damaged by an increase in intra-ocular pressure (IOP). One explanation of the damage is that the lamina cribrosa (LC) bends under the pressure and bends the ganglion cells in the outside of the LC. The ganglion cells coming from the periphery of the retina lie at the periphery of the LC and are bent more than those in the center of the LC, which are the ones coming from closer to the center of the retina. This extra bending causes extra stress on the ganglion cells, causing them to die early in glaucoma. This explanation accounts for the general observation that the typical glaucoma patient goes blind in the periphery first and the loss of vision narrows inward. Glaucoma also shows arcuate losses in clumps. The large diameter ganglion cells (M cells and some of the P cells) are the first to die off because for large diameter cells there is more stress on those cells as they go through the tight openings in the LC.

An FDT device picks up these losses in M cells, in particular, since those cells respond to contrast sensitivity, the illusion used in the FDT. The FDT is discussed in more detail hereinafter. These losses are found early in glaucoma because the large diameter M cells are the first to die off in glaucoma and they do not overlap in their dendrites, so there is no covering up by nearest M cell neighbors. After the ganglion cells start to die off, their corresponding areas in the LGN start to die off due to atrophy. Recent research showed loss in the LGN early in glaucoma corresponding to those areas where the lost ganglion cells projected. So, in the case of glaucoma, both ganglion cell loss and LGN loss appear to be caused by the increased IOP in the eye.

In Alzheimer's Disease (AD), there is no corresponding increase in IOP. In AD neurons degenerate due to other means. There is no bending of the LC and no loss of M cells early in AD from the LC. In normal individuals (also referred to as "normals"), all three pathways (M, P1, and P2 above) are intact. The nerve signal goes from the retina across pathway M to the LGN, then to the VC across P1, and finally back to the LGN across P2. Since there are no losses in any of the three pathways, the 80% feedback to the LGN from P2 correlates with what the LGN is receiving from M. There are no apparent losses anyway in the system.

However, in early stages of AD, amyloid plaques and tangles attack the neurons in the brain. They may be found in P1, P2, the VC, or any combination of those three. If they attack any of those three, then the signal going back to the LGN across P2 does not correlate with what is going to the LGN from the retina across M. The brain has difficulty correlating two signals that begin to become dissimilar as AD progresses, as compared to signals that it expects to be similar (based on years of normal neural activity). This response mimics a loss of M cells when observed using FDT methods, though this may not be a real loss of M cells in early stages of AD. As the disease progresses, the M cells likely atrophy because the LGN is not using the conflicting information from them. (There is a similar phenomena in the brain in ambliopia where higher parts of the brain are confused by the conflicting signals coming from the two eyes, so the brain shuts off the signal coming from one of the eyes causing that eye to atrophy over the first 6 years of life if the ambliopia is not corrected.)

One sees loss of gray matter in the brain in AD. Scientists have picked this up with both MRI and PET, as is discussed in more detail hereinbelow.

A lesion anywhere in the pathway can cause atrophy either upstream or downstream of the lesion. One should expect to see loss of gray matter first where the lesion is, then upstream or downstream from the lesion. In late stages of AD, researchers have found amyloid plaques and tangles even on the retina. The losses picked up by FDT when used with AD patients are not necessarily like those in glaucoma. AD losses can occur anywhere in the visual field since the apparent losses correspond to where the lesions are in the visual neuron pathway, which in principle can correspond to anywhere in the visual field. Hence the visual field losses in FDT are spottier than in glaucoma.

Similarly, the FDT can be used for multiple sclerosis (MS). It is known that MS affects neurons and that the effect comes and goes with time. There is apparent recovery of the cells at least in early stages of the disease. One would therefore expect the FDT diagnosed areas of loss in the visual field to move around the visual field over time, and perhaps to recovery temporarily. As the disease progresses to the point where there is a lot of loss on the retina, the areas of loss will remain lost and will not show temporary recovery.

The retina and brain do parallel processing to determine relative position of adjacent objects. In the case of dyslexia, this processing somehow gets reversed and the subject mixes up the order of letters in words or even the order of entire words. This too could show up as an apparent ganglion cell loss. Again, the apparent loss could be from the ganglion cells or from the feedback to the LGN.

The FDT represents a device to measure early stages of neurological disease and abnormalities, and to track changes over time. FDT has been shown to provide earlier detection with less variability than traditional visual field analysis as represented by the Humphrey HFA. FDT is non-invasive, fast, and accurate. It is easier to use than HFA and less expensive. The FDT can be a screener in the primary care doctor's office to screen and track neurological disease. FDT can be extended for use with many neurological diseases, in addition to glaucoma. This makes it a good screening tool for primary care.

The present invention provides an improved FDT apparatus for screening for many neuro-degenerative diseases, including Alzheimer's, non-Alzheimer's dementia, Parkinson's, multiple sclerosis, macular degeneration, ALS, diabetes, dyslexia, head trauma, and possibly others.

According to one feature of the invention, patients would be screened in the doctor's office or in other settings such as a commercial screening activity to get a baseline reading. A primary care physician would then either refer a patient to a specialist (if an abnormality is detected) or, if the screening results are initially within normal limits, watchfully wait for any progression by comparing results over time.

When a patient is referred to a specialist, the specialist might prescribe the 2 hour cognitive tests and/or an MRI or PET scan for a more definitive diagnosis. All of these tests are expensive and time consuming, so it is important to weed out normals with the improved apparatus prior to using these more expensive tests. The improved apparatus can comprise an FDT2 62-zone test, an input port for a PanOptic retinal camera, and a programmable computer and software recorded on a machine readable memory that when operating can differentiate various neurological disorders. The standard of care will be to screen for other neurological disorders beyond glaucoma and to differentiate which disorder is present.

The present FDT (such as FDT Matrix) works well in its present form for measuring apparent M cell losses in contrast sensitivity. In the improved apparatus, additional sensitivity/specificity are gained by optimizing the spatial frequencies, temporal frequencies, and/or color of the patterns used to also detect changes more specific to P cells or even K cells, i.e. all forms of retinal ganglion cells, projecting to different areas of the LGN.

The improved FDT device is expected to identify early stages of neuronal loss in the brain by picking up real losses of ganglion cells as well as apparent losses of ganglion cells as a result of the feedback loop to the LGN caused by damage to neurons in other places in the brain.

Recent Findings Relating to Other Medical Technologies

Testing on 6 normal individuals, 6 individuals with mild cognitive impairment (MCI), and 6 individuals with AD are expected to show a correlation between FDT measurements and early neuronal dysfunction (before neuronal loss or symptoms), using cognitive tests as a reference (e.g., "the gold standard"). It is further expected that MRI test results will show differences in volume of the hippocampus and entorhinal cortex, which are both areas associated with early cognitive dysfunction. MRI is expected to demonstrate that early damage to the pathways between the lateral geniculate nucleus (LGN) and the visual cortex (VC) in the brain can be identified using FDT testing. The attributes of the FDT are expected to include early or pre-symptomatic diagnosis accomplished with a relatively inexpensive device that performs tests in a short time (for example, 4 minutes vs. 90 minutes for a PET), which test is easily administered (compared to MRI or PET certification), and is non-invasive (compared to PET which uses a radioactive tracer).

MRI is a high resolution (1 mm), non-invasive differentiator of soft tissue, such as discriminating gray matter from white matter in the brain. MRI can measure volume loss from atrophy caused by amyloid plaques, but cannot image the amyloid plaques themselves. In addition, MRI spectroscopy involves differentiating metabolites by their resonant frequencies in a magnetic field gradient.

One may think of functional MRI (fMRI) as simply sequential MRI. For example, one can measure differences of oxygen level before and after a stimulus. Oxygen level increases with increased activity. It locates the parts in the brain where a particular function or stimulus is processed. A stimulus that the brain responds to causes changes in synapses, which increases the blood flow to an area where activity is occurring, which in turn increases the oxygen content, which causes a measurable change in the magnetic resonance image. Since fMRI measures brain activity, it can determine viability of sections of the brain. One can use stimulation of selected retinal areas to probe regions of the visual cortex that respond. An fMRI image can be presented as a structural MRI image with false color superposition to represent the level of activity in specific areas. However, fMRI cannot resolve such structures as 25 micron long capillaries having 0.5 micron diameter. Rather, it integrates the effects of all blood vessels in an area. One of the difficulties associated with fMRI is the possibility that areas of the brain can be accidentally stimulated.

Fluorodeoxyglucose positron emission tomography (FDG-PET) can be used to measure glucose metabolism. While its resolution is poor (3 to 8 mm), it is very sensitive to nano-molar quantities of neuro-transmitters and neuro-chemicals such as glucose and acetylcholene. It requires a radioactive tracer in the blood. It cannot be used to measure cognitive state because one must wait 60 to 90 minutes for everything except the FDG trapped in the active tissue to wash out of the area. According to some researchers, one can normalize a PET measurement by first doing a structural MRI to determine the amount of gray matter in each voxel.

Some researchers use radioactive carbon Pittsburgh compound B (PIB) as a marker that can be bound to amyloid in Alzheimer's (AD). Amyloid locates between neurons and tangles within neurons. Amyloid concentrates in pre-frontal and temporal cortex, but not in the visual cortex and the hippocampus. It is believed, however, that tangles locate in the hippocampus and entorhinal cortex early in AD. Amyloid plaques appear before clinical detection of AD, which suggests that earlier detection of AD can be accomplished by methods that permit the monitoring of such amyloid plaques.

It has been found by researchers that hypo-metabolism in the left hemisphere and visual cortex using PET can differentiate between frontal temporal dementia (FTD) and AD. It is expected that FDT can also differentiate FTD and AD.

Reduction in hippocampal volume has been shown to predict the conversion of MCI to AD. In addition, entorhinal cortex volume is 10% lower in pre-MCI individuals than in normal individuals and may therefore also be a predictor for conversion to AD. FDG-PET (glucose in cortex), amyloid imaging from PIB-PET, MRI measurement of hippocampal volume, or whole brain atrophy appear to be predictors of cognitive decline and dementia.

Some researchers suggest that microglial action creates cytokines when the brain is injured and this damages the nerves. The use of C-PK11195 bound to amyloid plagues in the thalamus and white matter has demonstrated earlier detection of amyloid than PET using PIB bound to amyloid, which appears to incorrectly suggest that the thalamus and VC are spared of amyloid in AD. While PIB used as a histologic stain on biopsied material permits identification of both amyloid and tangles, PIB-PET identifies amyloid, but not tangles in gray matter in AD. The posterior cingulated and frontal lobes retain more PIB in AD than in MCI, and more in MCI than in normals.

The progression of gray matter (cortex) loss in AD has been studied. Researchers have found 4 to 10% loss in hippocampal volume per year in AD compared to only 1.5% per year in normals.

MRI has been used to measure cortical thickness (gray matter) at many individual points in the brain. The cortical thickness varied from 1 to 5 mm. Researchers have measured 0.02 mm/year loss in thickness due to normal aging and 0.3 mm/year in AD. Researchers have also found loss in thickness of the VC, despite the fact that PET studies of amyloid suggest that the VC is spared in early AD. Cortical thinning of inferior temporal gyrate and para-hippocampal gyrate are suggested to give 100% sensitivity and 95% specificity in diagnosing AD.

It is known that higher magnetic fields, such 7T magnetic fields for MRI can be used to see much finer structure in all parts of the brain. It is also recognized that higher magnetic fields require more expensive magnets, and can present certain risks (such as the risk that objects that are not carefully and adequately secured may become missiles that are violently transported to the magnet).

Some researchers have used MRI to show tissue losses in the medial temporal lobe (hippocampus and entorhinal cortex) in early MCI and AD, as well as changes in the shape of these areas.

Some researchers have found that neuronal loss correlates well with atrophy of hippocampus volume. On average, loss starts at age 53 and progresses at different rates for normal (slowest), MCI, and AD (fastest) subjects. Decreases in hippocampal volume and in the entorhinal cortex can be identified in MRI . . . .

It is believed that the hippocampus is used in learning new information, such as associating a new name with a new face. Some researchers have found that there is a decrease in hippocampus activity in MCI, followed by a significantly greater activity decease in AD with a total loss of activity in late AD. The medial temporal lobe of the cortex showed a similar loss in activity in MCI, but showed a compensatory increase in activity in AD, but no one understands why this is true. The three areas of the brain most responsible for brain activity of learning new material such as a new name/face are the left pre-frontal cortex and both sides of the hippocampus. Old information appears to be spread out across the brain, rather than in those three specific areas.

Some researchers have found that the rates of change of volume of the hippocampus and entorhinal cortex accelerate with age, i.e. the loss is not linear. Hippocampus loses about 4 to 6% per year in AD, 2.5% in MCI, and 1.5% in controls. Likewise, entorhinal loss is about 7% per year in AD and 1.5% in controls.

It is expected that there is a correlation of FDT measurements with hippocampus and entorhinal loss. It is expected that losses identified using FDT methods are sensitive enough to show changes over time, including relatively short times such as one year. It is expected that volume alone of the hippocampus and entorhinal cortex will show differences between normal and severe AD.

According to some researchers, amyloid is present in all body fluids. It is produced in glial cells in the central nervous system. Apolipoprotein E ("ApoE") co-locates with amyloid in human brains and slows the clearing of amyloid from the central nervous system. Amyloid is present at low levels for many years, and then starts to form in more abundance, forming plaques faster if ApoE is present than if not. Enzyme-linked immunosorbent assay ("ELISA") can be used to test for the level of ApoE in a person's body.

Researchers have shown that hippocampal volume loss can predict which individuals will convert to AD. According to this research, brain volume is reduced 0.2% per year in normal aging, which is much slower than the hippocampal loss in AD.

It is expected that correlations will be determined among FDT measurements and medial temporal lobe (hippocampal and entorhinal cortex) volume, volume and shape of LGN and VC (for example determined by MRI), the progression of gray matter loss in the brain cortex of AD sufferers, and the early thinning of the cortex, particularly in the parahippocampus and VC.

Figure 13A:
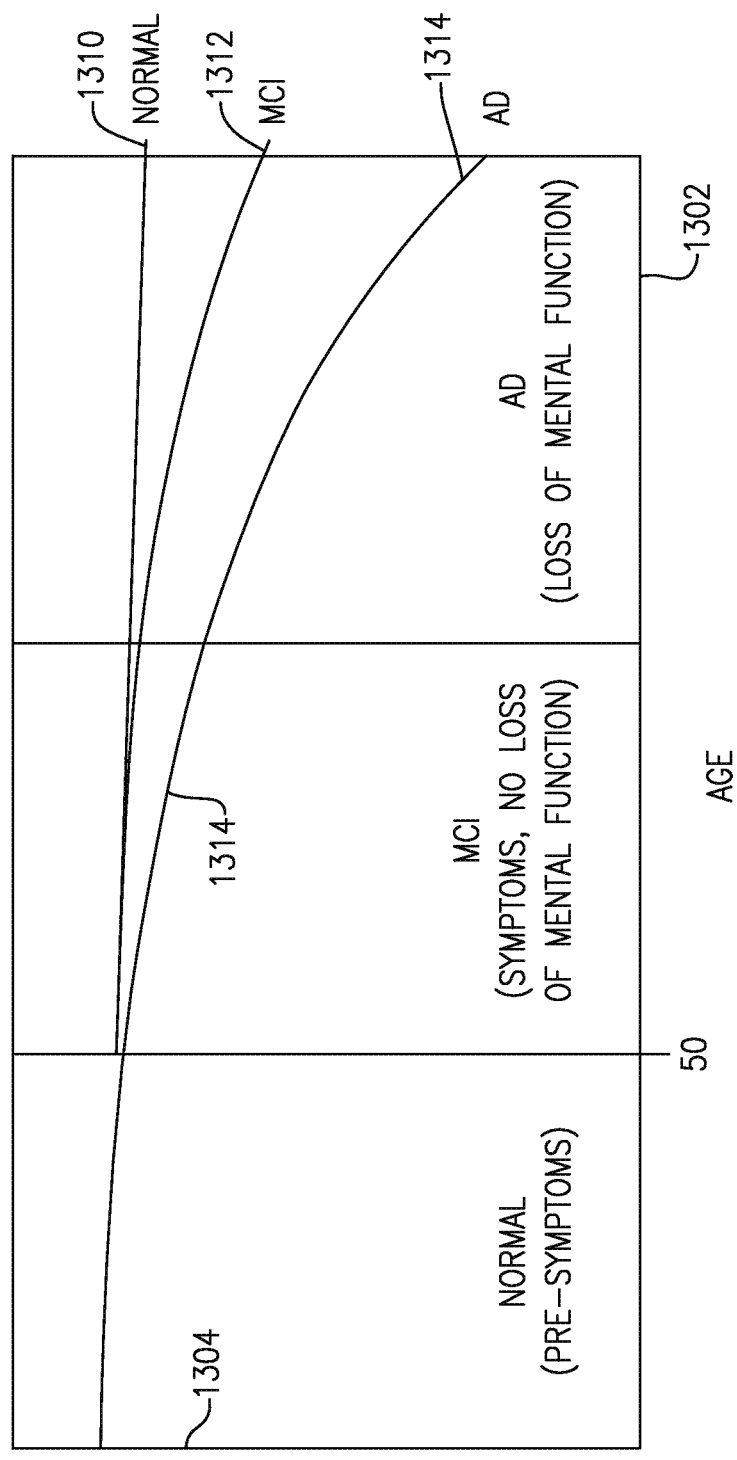
FIGS. 13A-13B are diagrams showing the time evolution of response to stimuli using several testing procedures.
Figure 13B:
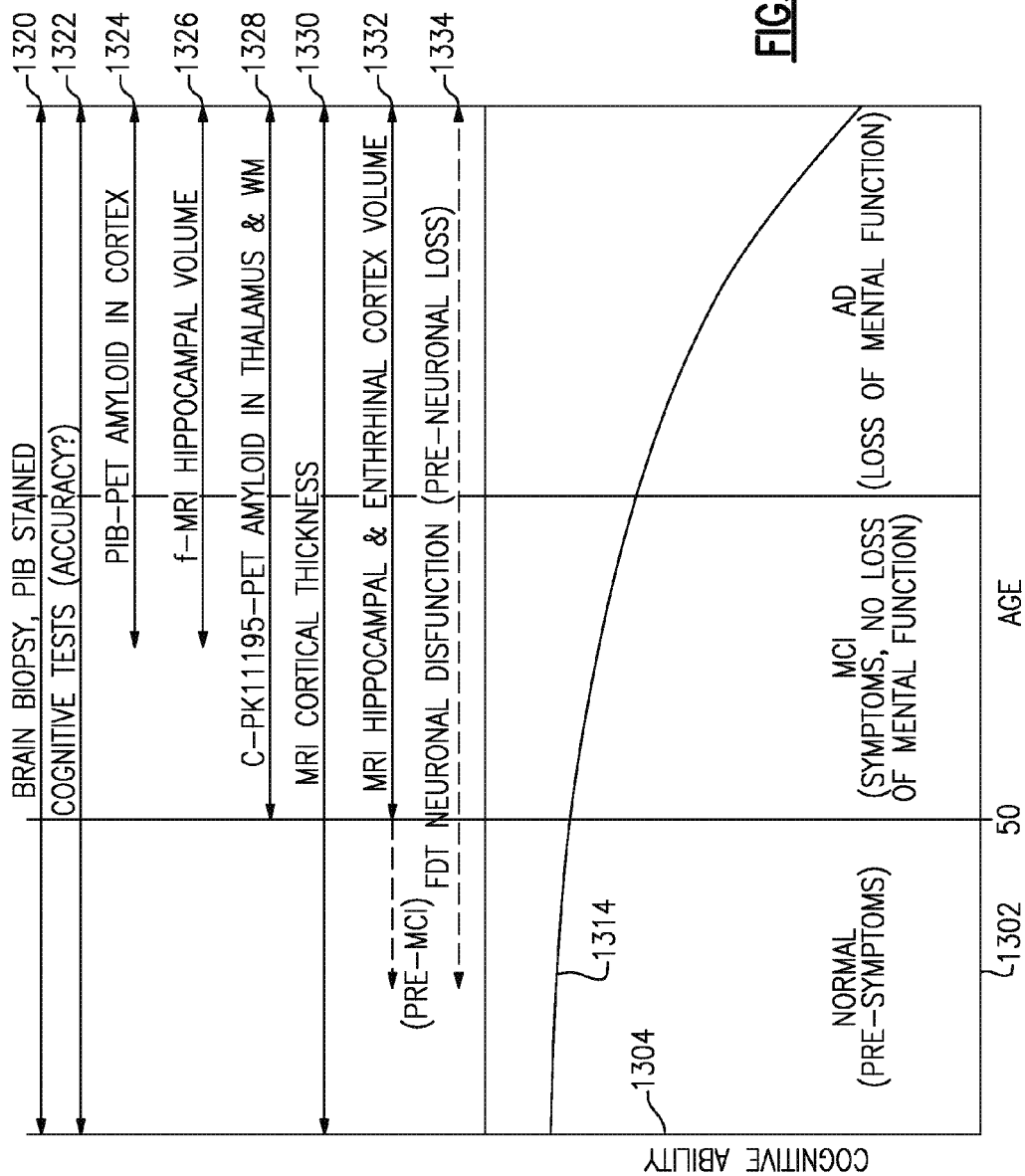

FIGS. 13A-13B are diagrams showing the time evolution of response to stimuli using several testing procedures. In FIG. 13A, the horizontal axis 1302 represents age in years of a person, and the vertical axis 1304 represents cognitive ability, with greater ability represented by points that are more distant from the horizontal axis 1302. In FIG. 13A there are sown three regions, labeled from left to right "Normal", "MCI," and "AD." In FIG. 13A, a dividing line appears at an age of approximately 50 years between the "Normal" and "MCI" regions. Three curves are also present in FIG. 13A. A first curve 1310 represents normal behavior with respect to cognitive ability over time (e.g., little or no diminution in cognitive ability over time). A second curve 1312 represents the cognitive behavior with respect to time for a person with mild cognitive impairment, and that curve shows some diminution in cognitive ability with time. A person suffering from MCI may show some symptoms of impairment, but there appears to be little or nor loss of mental function. A person presenting with AD is expected to exhibit a cognitive ability curve similar to 1314, in which the loss of cognitive ability is more severe. In AD sufferers, loss of mental function is typically observed. The significance of the curves in FIG. 13A is that one may be able to provide an interpretive result indicating whether a person has or is susceptible to getting MCI or AD. Similarly, other relationships can provide a similar interpretive result indicating the likelihood that a person is susceptible to or the fact that a person is already beginning to exhibit another disease.

In FIG. 13B, the axes 1302 and 1304 have the same significance as in FIG. 13A, and a curve 1314 for a typical person presenting with AD is shown. At the top of FIG. 13B, the arrows 1320-1334 are provided to show when in the development of a disease condition the various tests that have been described are able to provide meaningful data. Arrow 1320 represents a brain biopsy test, in which the tissue is stained with PIB. This test can be preformed meaningfully at any time, but it is invasive. Arrow 1322 represents cognitive tests, which can also be performed at any time, but which also are subject to some variability and may not be extremely accurate for small percentages. Arrow 1324 represents PET scans with PB3 to look for amyloid in the cortex. These tests become effective at times after the clear inset of cognitive loss, possibly because by their expensive and invasive nature, they are not performed on people who appear to be normal. Similarly, fMRI tests as represented by arrow 1326 become effective at times after the clear inset of cognitive loss. Arrow 1328 is representative of research results showing that C-PK1119-PET tests can indicate the presence of amyloid in the thalamus and the white matter. Arrow 1330 represents MRI cortical thickness measurements which can be performed at any time, but which are also expensive. Arrow 1332 represents MRI tests of hippocampal and entorhinal cortex volume. Arrow 1334 is representative of the FDT tests to discover neuronal dysfunction as described as embodiments of the present invention. As is seen, the tests according to the principles of the present invention can begin before a person becomes symptomatic, and before any appreciable loss of mental function has taken place.

FDT Apparatus

Some researchers believe that the FDT measures the loss of M cells in general, but does not measure $M.sub.y$ cell loss. FDT measures a "cortical loss of temporal phase discrimination". FDT can be viewed as a probe of contrast sensitivity of the magnocellular ("MC") pathway. As has been expressed by researchers in the field, FDT measures the "reduced cortical sensitivity to the temporal phase of achromatic counter-phased gratings."

FDT is a good screener for early glaucoma and a low-variability trend analyzer. In glaucoma, FDT measures the loss of M cells, which loss appears to be caused by bending of large diameter cells by the displaced lamina cribrosa caused by elevated IOP and/or weak lamina cribrosa structure, starting in the periphery or more sporadically in scotomas. FDT can be used to measure the influence of these cells (or their progressive loss) on cortical phase discrimination downstream in the brain.

In other forms of neurological disorders, the FDT measures a loss of cortical phase discrimination, but not from M cell loss caused by increased IOP and lamina cribrosa displacement. Instead, FDT is measuring the loss in cortical response due to other causes. For example, in Alzheimer's disease (AD), the apparent loss is likely coming from neuron loss somewhere in the pathway from lateral geniculate nucleus (LGN) to visual cortex (VC) and the feedback to the LGN (paths $P.sub.1$ and $P.sub.2$ in FIG. 12). Amyloid plagues and tangles attack these pathways in AD. The effect is one of apparent loss of M cells, but it is believed that the loss in the pathways may actually occur further back in the brain. The actual damage is to the neurons in the brain, but the damage is manifest as a FDT-measured loss in contrast sensitivity. The visual cortex is still impaired in its ability to discriminate temporal phase.

The actual damage from the plaques and tangles could be located anywhere in the nervous system associated with vision, including the retina, the M cells, the LGN, path $P_1$, the VC, or path $P_2$. In early stages of AD, the plaques most likely occur in $P_1$, VC, or $P_2$. In later stages of AD, plaques have been found on the retina and, of course, in the brain as substantiated by autopsies. It is almost immaterial where the damage is done since the result is the same: the person suffering from these kinds of damage to the nervous system associated with vision scores an abnormal FDT test.

Parkinson's, multiple sclerosis (MS), and other neurological diseases have some similarity to AD, yet they are different and have different underlying features. The optimum parameters for measuring each disorder with FDT may have different values, such as different special frequency, temporal frequency, number and size of zones, and color of the patterns that are effective in disclosing the disease condition. Each of these disorders can be identified by the FDT test. It is important to differentiate abnormal FDT responses from normal responses indicative of normal health. In addition, it is possible to differentiate among disorders through optimization of the FDT test and the analysis of patterns of loss. As an example, MS will show as more spotty losses in the field. These losses will come and go until they stabilize at later stages in the disease. By comparison, in patients experiencing Parkinson's disease, the loss in vision is a more diffuse loss than either AD or MS. In addition, it is expected that correlation among cognitive tests, MRI gray matter loss in the brain, and specific diseases, such as AD, exist.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein.

While the present invention has been explained with reference to the structure disclosed herein, it is not confined to the details set forth and this invention is intended to cover any modifications and changes as may come within the scope of the following claims.

What is claimed is:

1. An apparatus for performing multiple procedures involving the eye, the apparatus comprising:
    an imager for imaging at least a portion of an eye of a patient, the imager configured to provide image data;
    a data collection apparatus for collecting a data set corresponding to at least a portion of an eye of a patient, the data collection apparatus configured to provide said data set that is indicative of a neurological disorder; and
    a data analysis module that interrelates the image data and the data indicative of a neurological disorder to provide an interpretive result.

2. The apparatus as recited in claim 1, wherein the image data comprising a data type selected from the group consisting of data from ophthalmic images using confocal microscopy data, retinal polarimetry data, optical coherence tomography data, thermal image data, spectroscopic image data, refractometry data, and visible image data.

3. The apparatus as recited in claim 1, wherein the neurological disorder is selected from the group consisting of glaucoma, macular degeneration, diabetic retinopathy, Parkinson's disease, Alzheimer's disease, dyslexia, multiple sclerosis, optic neuritis, LDS, head trauma, diabetes, and inappropriate responses to contrast sensitivity patterns.

4. The apparatus as recited in claim 1, further comprising a display module that provides a display of analyzed data to a user.

5. The apparatus as recited in claim 1, further comprising a report module that reports the interpretive result.

6. The apparatus as recited in claim 1, further comprising an output module that reports the interrelated data from the image data, the data indicative of a neurological disorder and the interpretive result.

7. The apparatus as recited in claim 1, further comprising a superposition module for superimposing data obtained from an image and data indicative of a neurological disorder.

8. The apparatus as recited in claim 7, further comprising a display for displaying the superimposed data obtained from the image and the data indicative of a neurological disorder.

9. The apparatus as recited in claim 1, further comprising a memory for storing data, the data comprising at least one of image data and data indicative of a neurological disorder.

10. The apparatus as recited in claim 9, wherein the memory for storing data is configured to store and to selectively retrieve data for determining changes induced in response to an applied stress.

11. The apparatus as recited in claim 10, where the applied stress is selected from the group consisting of intra ocular pressure variation, blood pressure variation, oxygen concentration variation, exercise, flashing light, drug administration, administration of insulin, and administration of glucose.

12. The apparatus as recited in claim 1, further comprising means for aligning the image of the eye of a patient.

13. The apparatus as recited in claim 12, wherein the alignment means operates automatically based on the movement of the eye of a patient relative to the imaging means.

14. The apparatus as recited in claim 1, further comprising means for performing at least one objective eye-related interpretive procedure.

15. The apparatus as recited in claim 1, wherein the apparatus displays to an eye of a patient a test pattern comprising a fixation signal and a moving pattern during an OKN procedure.

16. The apparatus as recited in claim 1, wherein the data analysis module is configured to automatically determine a presence of an abnormality.

17. The apparatus as recited in claim 16, wherein the data analysis module comprises a scaling module for providing a scaled estimation of an extent of the abnormality.

18. The apparatus as recited in claim 1, further comprising an information input module for inputting other patent-related information including at least one from the group of tonometer intraocular pressure, patient-history, family history, blood pressure, vital signs, medication and pupillometry.

19. A method of treating a patient, comprising the steps of:
    performing an examination of a patient using the apparatus of claim 1; and
    treating said patient based at least in part on a result obtained from said examination.

20. The method of treatment of claim 19, further comprising the step of providing the treatment based at least in part on information stored in a memory.

21. The apparatus of claim 1 wherein said data set is indicative of an abnormality appearing to involve a retinal portion of the eye.

22. The apparatus of claim 21 wherein said abnormality actually involves, at least in part, an abnormality of the brain.

23. The apparatus of claim 1 where said data set includes at least a first data type that is visible image data and a second data type that is data indicative of an inappropriate response to contrast sensitivity patterns.

24. The apparatus of claim 23 wherein a combination of said first data type and said second data type is interrelated to indicate a presence of glaucoma or Alzheimer's disease.

* * * * *